(12) United States Patent
Baucom

(10) Patent No.: US 10,018,612 B2
(45) Date of Patent: Jul. 10, 2018

(54) RUGGEDIZED SOIL SAMPLER FOR ROUGH TERRAIN SAMPLING WITH ROW CLEANING CAPABILITY

(71) Applicant: Allan L. Baucom, Monroe, NC (US)

(72) Inventor: Allan L. Baucom, Monroe, NC (US)

( * ) Notice: Subject to any disclaimer, the term of this patent is extended or adjusted under 35 U.S.C. 154(b) by 57 days.

(21) Appl. No.: 15/269,215

(22) Filed: Sep. 19, 2016

(65) Prior Publication Data

US 2018/0080914 A1   Mar. 22, 2018

(51) Int. Cl.
*G01N 3/02* (2006.01)
*G01N 33/24* (2006.01)
*G01N 1/08* (2006.01)

(52) U.S. Cl.
CPC ............... *G01N 33/24* (2013.01); *G01N 1/08* (2013.01); *G01N 2033/245* (2013.01)

(58) Field of Classification Search
CPC .. G01N 2030/027; G01N 30/06; G01N 30/16; G01N 30/20; G01N 30/02
USPC .................................. 73/864.41, 61.55, 863
See application file for complete search history.

(56) References Cited

U.S. PATENT DOCUMENTS

| | | | |
|---|---|---|---|
| RE30,901 E * | 4/1982 | Boxrud ................ | G01N 1/08 172/22 |
| 4,869,115 A * | 9/1989 | Edwards ................ | G01N 1/04 172/112 |
| 5,211,248 A * | 5/1993 | Nosewicz ................ | E21B 1/02 173/28 |
| 5,419,211 A * | 5/1995 | Rodel ................ | E21B 10/02 73/864.44 |
| 5,435,399 A * | 7/1995 | Peterson ................ | E02D 1/04 175/135 |
| 5,887,491 A * | 3/1999 | Monson ................ | A01B 79/005 250/253 |
| 6,363,803 B1 * | 4/2002 | Hubers ................ | E21B 49/02 175/19 |
| 7,827,873 B2 * | 11/2010 | Burton ................ | E21B 7/027 173/19 |
| 8,613,234 B1 * | 12/2013 | Harrell ................ | G01N 1/08 172/22 |
| 8,677,808 B2 * | 3/2014 | Ozbal ................ | G01N 30/24 210/198.2 |
| 8,683,879 B2 * | 4/2014 | Tomita ................ | G01N 30/16 134/166 R |

(Continued)

*Primary Examiner* — Eric S McCall
*Assistant Examiner* — Mohammed E Keramet-Amircola
(74) *Attorney, Agent, or Firm* — William G. Sykes

(57) ABSTRACT

A soil sampling apparatus consisting of a sample collection drum having a tapered probe for extracting soil plugs that are discharged by gravity into the drum. A row clearing apparatus may be disposed forward of the probe. As drum rotates, soil plugs are mixed and, when mixed, are discharged into a sample a removable container in a removable tray on a carousel. Prior to loading sample containers into the tray, a unique bar code is affixed thereto. A bar code reader tracks each container and information regarding each sample is stored by an electrical/electronic controller. GPS information from an onboard GPS system is included in the stored data. Stored data may be immediately transmitted or, alternately batch uploaded to a remote site. A communications controller typically provides cellular and Wi-Fi communications. The electrical/electronic controller is used to control all aspects of the soil sampler.

15 Claims, 21 Drawing Sheets

(56) References Cited

U.S. PATENT DOCUMENTS

| | | | | |
|---|---|---|---|---|
| 9,116,078 | B1* | 8/2015 | Scheiderer | G01N 1/04 |
| 9,200,492 | B2* | 12/2015 | McGraw | E21B 25/00 |
| 9,534,464 | B1* | 1/2017 | Kelley | G01N 1/04 |
| 2005/0172733 | A1* | 8/2005 | Drummond | A01B 79/005 |
| | | | | 73/864.41 |
| 2005/0252312 | A1* | 11/2005 | Garel | G01N 1/08 |
| | | | | 73/863.82 |
| 2009/0178853 | A1* | 7/2009 | Pavlik | E21B 7/027 |
| | | | | 175/84 |
| 2012/0024744 | A1* | 2/2012 | Harrison | A01N 59/00 |
| | | | | 206/524.1 |
| 2012/0149623 | A1* | 6/2012 | Li | C09G 1/16 |
| | | | | 510/214 |

* cited by examiner

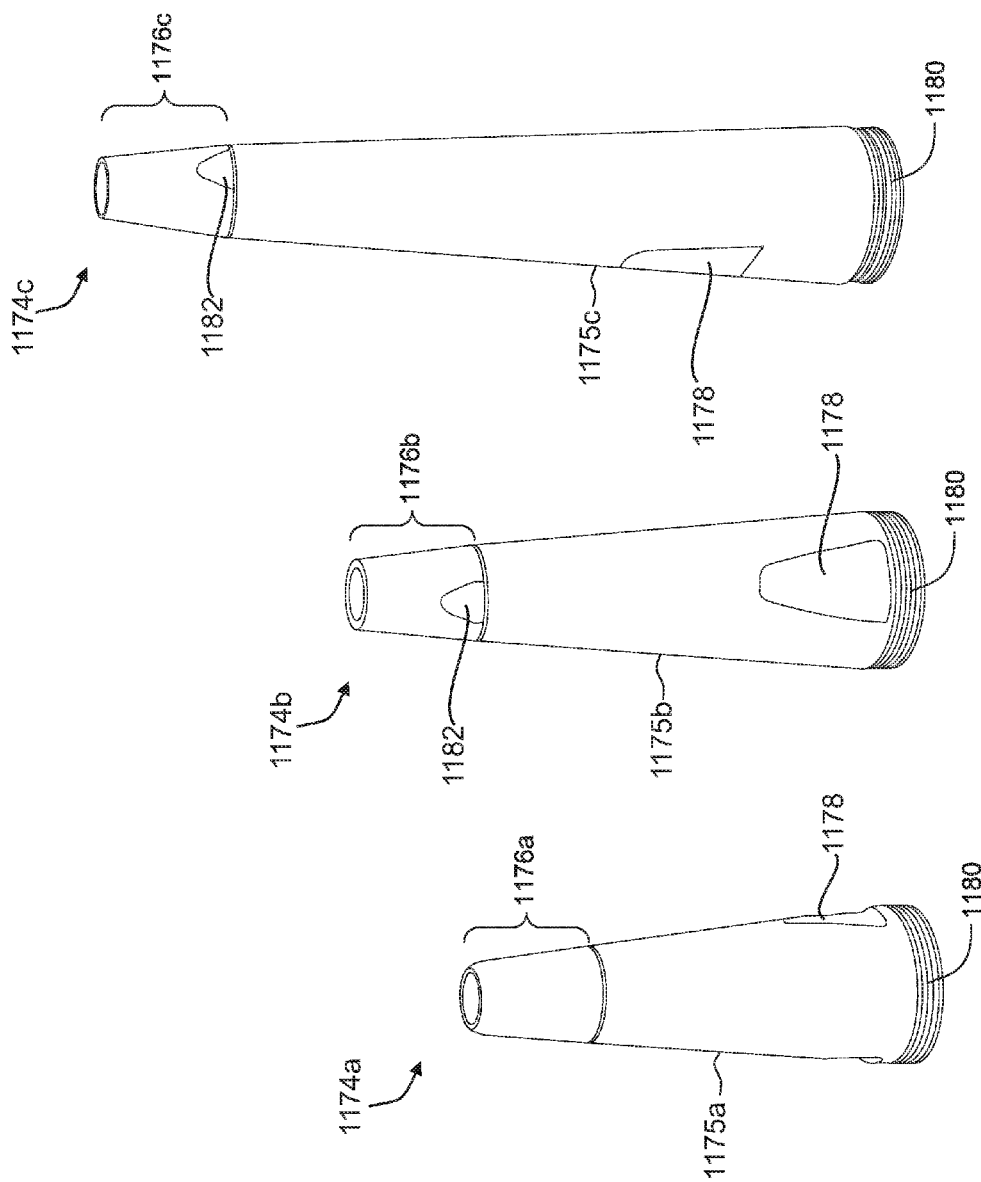

RUGGEDIZED SOIL SAMPLER FOR ROUGH TERRAIN SAMPLING WITH ROW CLEANING CAPABILITY

RELATED APPLICATIONS

This application is related to U.S. patent application Ser. No. 13/379,491 filed Jan. 3, 2012 for SOIL SAMPLING APPARATUS, now issued as U.S. Pat. No. 8,613,234, issued Dec. 24, 2013 to Linn Harrell and included herein in its entirety by reference.

FIELD OF THE INVENTION

The invention pertains to soil samplers and, more particularly, to ruggedized semi-automatic soil sampler for pulling across rough terrain by a truck or the like, the soil sampler having selective row clearing capability.

BACKGROUND OF THE INVENTION

Agronomy is the branch of agriculture dealing with field-crop production and soil management. Modern field crop farming relies on precision treatment of the soil. However, no soil treatment is possible before soil analysis indicates the precise treatment required.

The types of soil and climate in a given area, determine to a great extent, the kind of farming and the various crops that can be successfully grown at such location. Within any given area there are many kinds of soil having certain properties that require different land practices based on the residual and natural level of fertility. Because of these inherent variations, soil analysis has become a highly specialized field of endeavor for the chemical and fertilizer industry. Through research and experimentation these specialists have come to know what to expect of different types of soil and how to best supplement each particular type to produce maximum crop yield.

A good laboratory soil test and recommendation is primarily predicated on a reliable soil sample. Said test and any recommendations derived therefrom are only as reliable and accurate as the composite sample taken from the soil strata. Conversely, a poor soil sample can result in recommendations which are misleading to the producer and can cause lower yields due to the improper use of supplements. Before discovery of the subject invention, the conventional method of taking soil samples has been by the use of a clean bucket and a spade or by the use of a simple soil auger. Such methods are laborious, expensive, and time consuming and to say the least, not always reliable as the sampling operation is in such instances always subject to the element of error on the part of the sampler.

One previous attempt to provide a partially mechanizes soil sampling apparatus is disclosed in U.S. Pat. No. 8,613,234, issued Dec. 24, 2013 to Linn Harrell for SOIL SAMPLING APPARATUS.

HARRELL teaches rudimentary versions of some steps of soil sampling but requires large numbers of manually performed steps before soil samples are acquired. A driver of the tow vehicle must leave the cab frequently to affect many of the required soil sampling operations.

It would, therefore, be desirable to refine and automate many of the soil sampling steps required by the HARRELL apparatus to make an efficient, highly automate soil sampling device.

DISCUSSION OF THE RELATED ART

Attempts may be found in the prior art to provide some aspects of the present invention. For example, U.S. Reissue Pat. No. RE 30,901 for SOIL SAMPLING DEVICE, reissued Apr. 13, 1982 to Phillip P. Boxrud teaches a device for attachment to the drawbar of a tractor or similar vehicle for removing cores of soil from the ground. A plurality of hollow probes is mounted on the perimeter of a drum that may be lowered by a hydraulic cylinder to make contact with the ground. As the drum rotates, core samples are removed from the ground and deposited into the interior of the drum.

The RE 30,901 patent to BOXRUD is not seen to teach or suggest the novel soil sampling apparatus of the present invention.

SUMMARY OF THE INVENTION

In accordance with the present invention there is provided a soil sampling apparatus consisting of a semi-automatically controlled hollow, ground-contacting sample collection drum having a one or more hollow, tapered probe projecting outwardly from a central perimeter of the sample collection drum. The probes are communicative with an interior region of the sample collection drum and serve to extract soil plugs from the ground as the sample collection drum rolls therealong. Each soil plug is discharged by gravity from the probe and falls into the interior of the sample collection drum. As the sample collection drum rotates, all soil plugs are mixed with each other within the sample collection drum.

Once soil plugs from the desired area are collected, the sample collection drum is automatically raised. The sample collection drum is then rotated by an electric motor through an overridable clutch to continue to blend the collected individual soil samples. A sample collection funnel is then automatically inserted into an opening in the side of the sample collection drum. As the sample collection sample collection drum continues to rotate, the blended soil sample falls from the top of the sample collection drum into the sample extraction funnel.

The blended sample slide down the sample extraction funnel and is deposited into a removable sample collection cup retained in a sample cup receptacle disposed on the upper surface of a horizontal circular platform forming a part of a soil collection carousel assembly.

Once the blended soil sample is in the collection cup, the horizontal circular platform is rotated to bring a new, empty sample collection cup into position to receive the next blended sample.

The soil sample assembly is mounted on a trailer and may be pulled behind a truck or tractor. All functions are remotely controlled from the cab of the truck, tractor, or similar vehicle.

Prior to insertion into a sample cup receptacle, a unique machine-readable code, typically a bar code is applied or attached to each sample collection cup. An onboard bar code reader tracks each marked sample collection cup and as a sample is placed into each sample collection cup, information regarding each sample is stored by a dedicated electrical/electronic controller located on the soil sample. Typically GPS information from an onboard GPS system is included in the stored data. Stored data may be immediately transmitted or, alternately batch uploaded to a remote site. The electrical/electronic controller is used to control all aspects of the soil sampler.

It is, therefore, an object of the invention to provide a mobile, automatic soil sampling apparatus for removing multiple soil samples from a traversed area.

It is another object of the invention to provide a mobile, automatic soil sampling apparatus comprising a sample collection drum and at least one tapered soil sampling probe connected thereto.

It is an additional object of the invention to provide a mobile, automatic soil sampling apparatus wherein a sample collecting drum is automatically movable between a lowered, sampling position and a raised, travel position.

It is a further object of the invention to provide a mobile, automatic soil sampling apparatus wherein multiple samples from a desired sampling area are blended and then collected in a container.

It is an additional object of the invention to place a machine readable marking on each collection container.

It is yet another object of the invention to store data associated with each collected sample, typically including GPS data for the area from which sample was collected.

It is a still further object of the invention to provide a mobile, automatic soil sampling apparatus wherein multiple, selectable soil sample containers are provided and multiple areas, each producing a unique blended sample, may be sampled without human intervention.

It is yet another object of the invention to provide a mobile, automatic soil sampling apparatus wherein all operations involved are controlled by an onboard electrical/electronic controller.

It is another object of the invention to provide a mobile, automatic soil sampling apparatus wherein a television camera is disposed to remotely monitor operation of the soil collection apparatus.

It is an additional object of the invention to provide a mobile, automatic soil sampling apparatus wherein soil sampling probes are cleaned during each revolution of the sample collection drum.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 6A-1 to 6A-3 are side perspective, schematic views of three sampling probes of different lengths;

DETAILED DESCRIPTION OF THE PREFERRED EMBODIMENT

The present invention provides a ruggedized, semi-automatic soil sampler for removing periodic sample at a predetermined depth as the apparatus is pulled across a field or the like. All samples are automatically logged and GPS coordinates (e.g., "Lat/Lon") is recorded for each sample. After a predetermined number of samples has been acquired and thoroughly mixed, the composite sample is placed in a pre-labeled container. Sample containers are held in carousel trays and both empty and full carousels may be stored "on board" in a storage cabinet.

As used herein, the terms front, back, right, and left are with respect to the driver's seat of a tow vehicle to which soil sampler 1000 is attached.

Figure 1A:
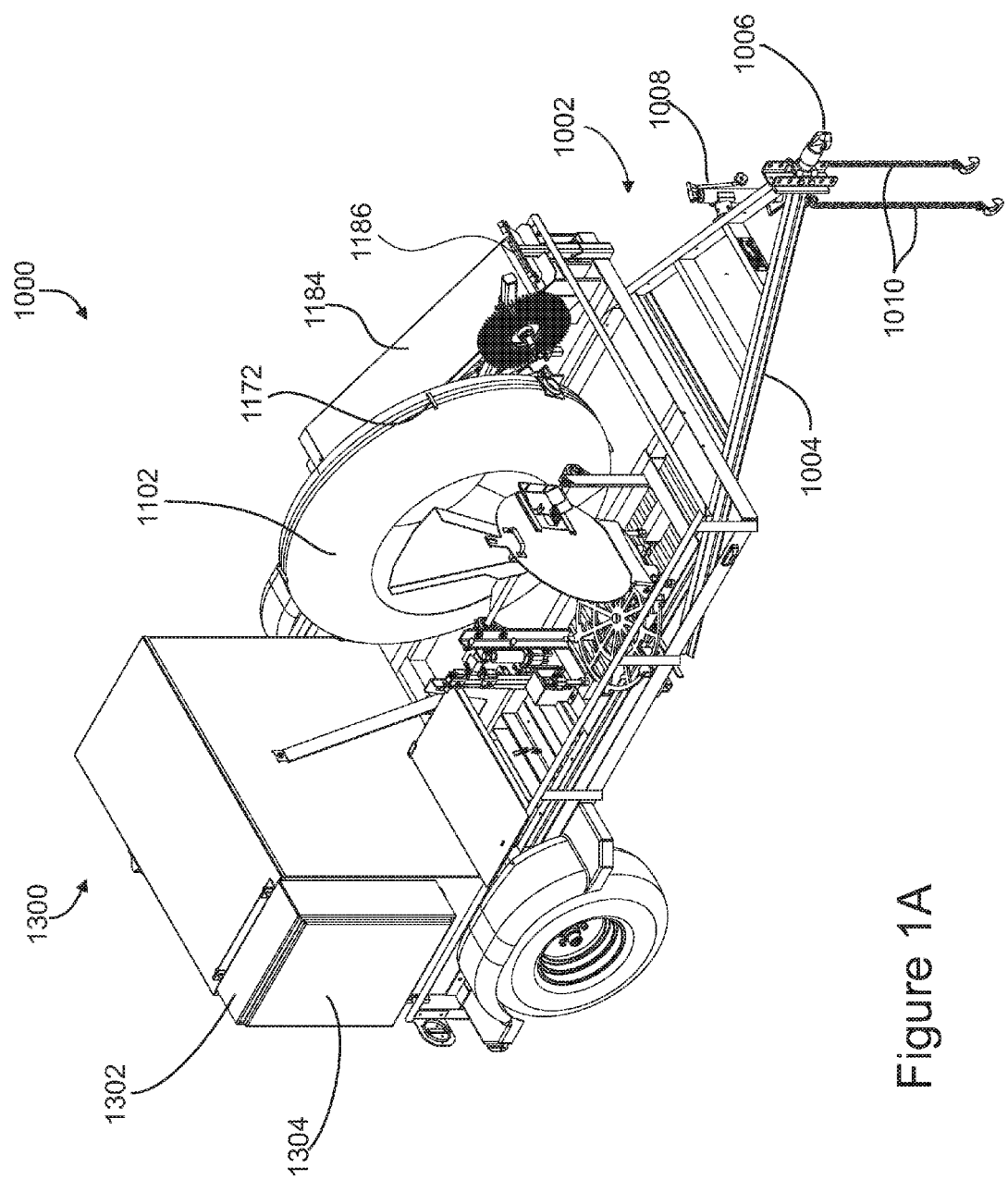
FIG. 1A is a right front perspective, schematic view of a soil sampler in accordance with the invention.
Figure 1B:
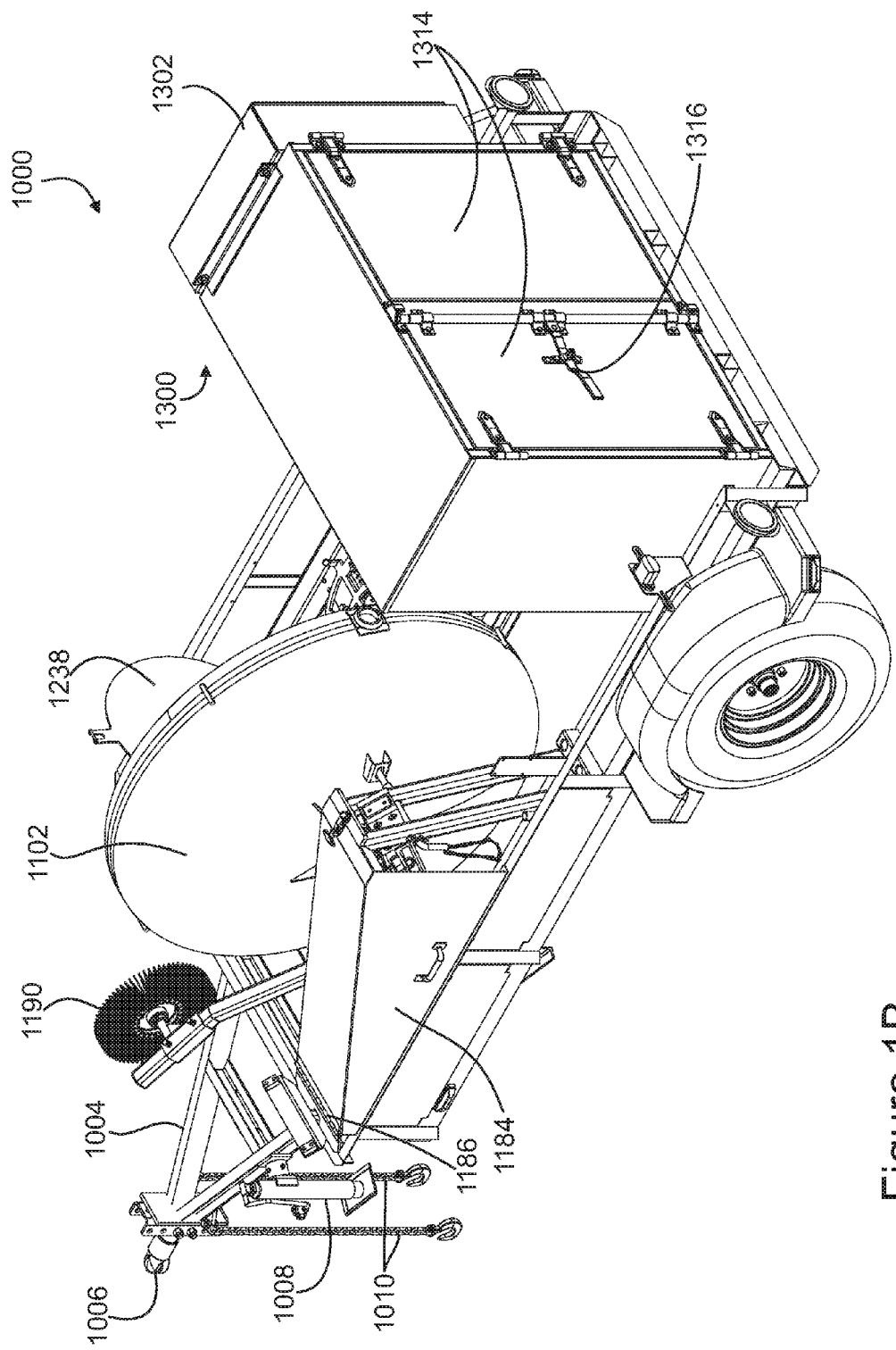
FIG. 1B is a left rear perspective, schematic view of the soil sampler of FIG. 1A.

Referring first to FIGS. 1A and 1B, there are shown right front and left rear perspective, schematic views, respectively, of a soil sampler in accordance with the invention, generally at reference number 1000. Several of the major functional sub-systems and components of soil sampler 1000 are identified in FIGS. 1A and 1B. Each sub-system and/or component is discussed in detail hereinbelow.

Soil sampler 1000 is built on a custom trailer frame 1002. Details of the trailer frame 1002 construction are discussed in more detail hereinbelow. Prominent in FIGS. 1A and 1B are trailer tongue 1004, hitch 1006, and tongue support jack 1008.

Figure 1C:
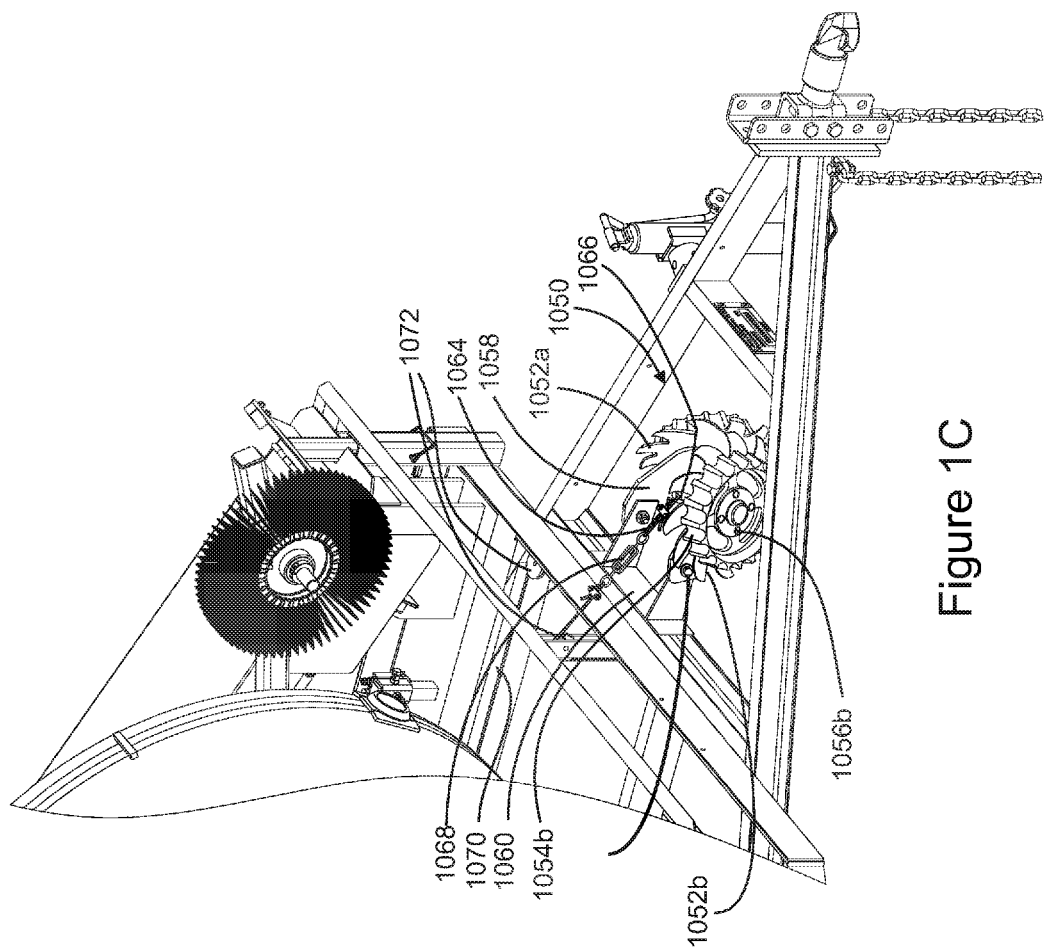
FIG. 1C is a detailed perspective, schematic view of a row clearing apparatus in place on the soil sampler.

Referring now also to FIG. 1C, there is shown a detailed perspective, schematic view of an optional row clearing apparatus apparatus 1050 attached to a horizontal cross member, not specifically identified, in the A-frame region tongue 1004 of soil sampler 1000.

Row cleaning apparatus is a modified version of a commercially available device from Yetter Manufacturing Co. of Colchester, Ill. as Catalog No. 2967-029 that has been found suitable for the intended application.

Row clearing apparatus 1050 has left and right rotating "shark" wheels 1052a, 1052b set apart from one another and inclined with respect to a vertical axis, not shown. Teeth, not specifically identified, disposed around the perimeter of shark wheels 1052a, 1052b engage the ground ahead of sampling probe 1174a, 1174b, 1174c, best seen in FIGS. 6A-1, 6A-2 and 6A-3 respectfully, to allow sampling probe 1174a, 1174b, 1174c easier access to the ground from which soil samples are being extracted.

Several variations of shark wheels 1052a, 1052b are available including tapered tooth and beveled wheel versions, these may be used interchangeably. The use of the term shark wheels is intended to include these any other variations in blade configurations.

Left and right floater wheels 1054a, 1054b, respectively, are mounted on an axle, not specifically identified, adjacent to and outboard from shark wheels 1052a, 1052b.

Finally, hubs 1056a, 1056b are mounted to the axle outboard from respective floater wheels 1054a, 1054b.

The axle with attached shark wheels 1052a, 1052b, floater wheels 1054a, 1054b, and hubs 1056a, 1056b is mounted in a so-called combo arm 1058. Combo arm 1058 is rotatively attached to a fixed bracket 1060 at pivots 1062. As a result of this mounting arrangement, row clearing apparatus 1050 may be raised and lowered.

An attachment eye 1066 is added to row clearing apparatus 1050 to which a short attachment cable 1064 is fastened using a cable clamp believed to be well known to those of skill in the art. Consequently, the cable clamp is not further discussed herein. It will be recognized any suitable mechanism or technique may be use to connect the ends of short attachment cable 1064 after passing through a first end, not specifically identified, of turnbuckle 1066.

A lift cable 1070 is affixed to a second, opposing end, not specifically identified, of turnbuckle 1068. Lift cable 1070 is routed around one or more pulleys 1072 until a distal end of lift cable 1070 is attached to raiseable drum support arm 1130 best seen in FIG. 3. This arrangement automatically lowers row clearing apparatus apparatus 1050 when sample collecting drum 1102 is lowered to its operative position.

It will be recognized that alternate arrangements to selectively raise and lower row clearing apparatus apparatus 1050. These included electrically-driven mechanisms or hand-operated winch system. Such mechanisms are believed to be well understood by those of skill in the art and, consequently, are not further described or discussed herein.

Figure 3:
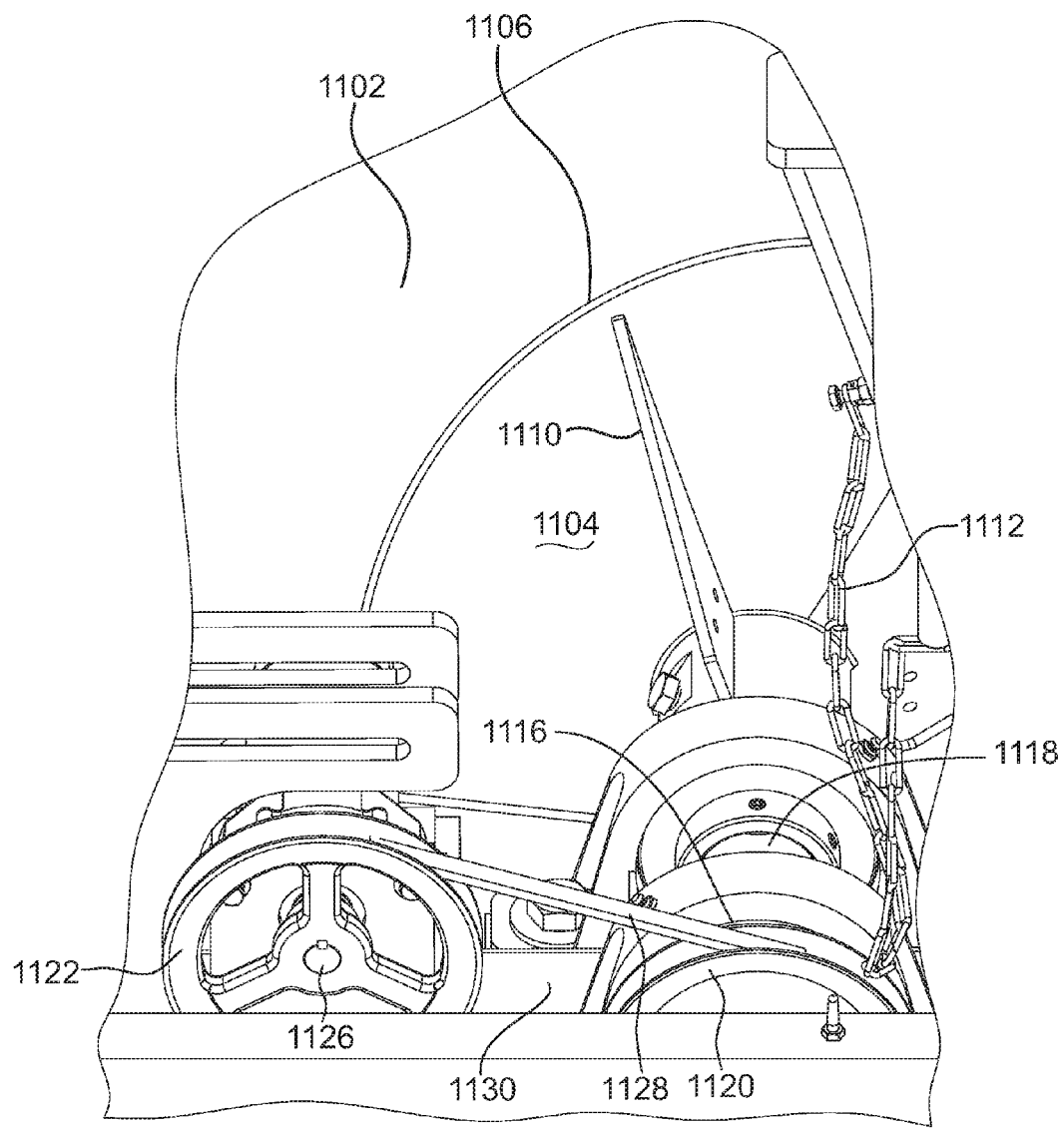
FIG. 3 is a detailed left side elevational, schematic view of a portion of the drum drive mechanism of FIG. 2.

Row clearing apparatus 1050 serves to clear any debris present in the path of sampling probes 1174a, 1174b, 1174c (FIG. 6A-1-6A-3). Any debris is moved to the sides of shark wheels 1052a, 1052b, consequently preventing sampling probes 1174a, 1174b, 1174c connected to sample collection drum 1102 from riding on crop residue or the like that might prevent sampling probes 1174a, 1174b, 1174c from being properly inserted into the soil profile that could result in an incomplete soil profile sample.

As may readily be seen in FIG. 1B, a storage cabinet 1300 is disposed at the rear of trailer 1002. A pair of hinged doors 1314 open to access storage, primarily for sample collection trays 1212 (FIG. 8B). A latch 1316 secures hinged doors 1314.

Figure 8A:
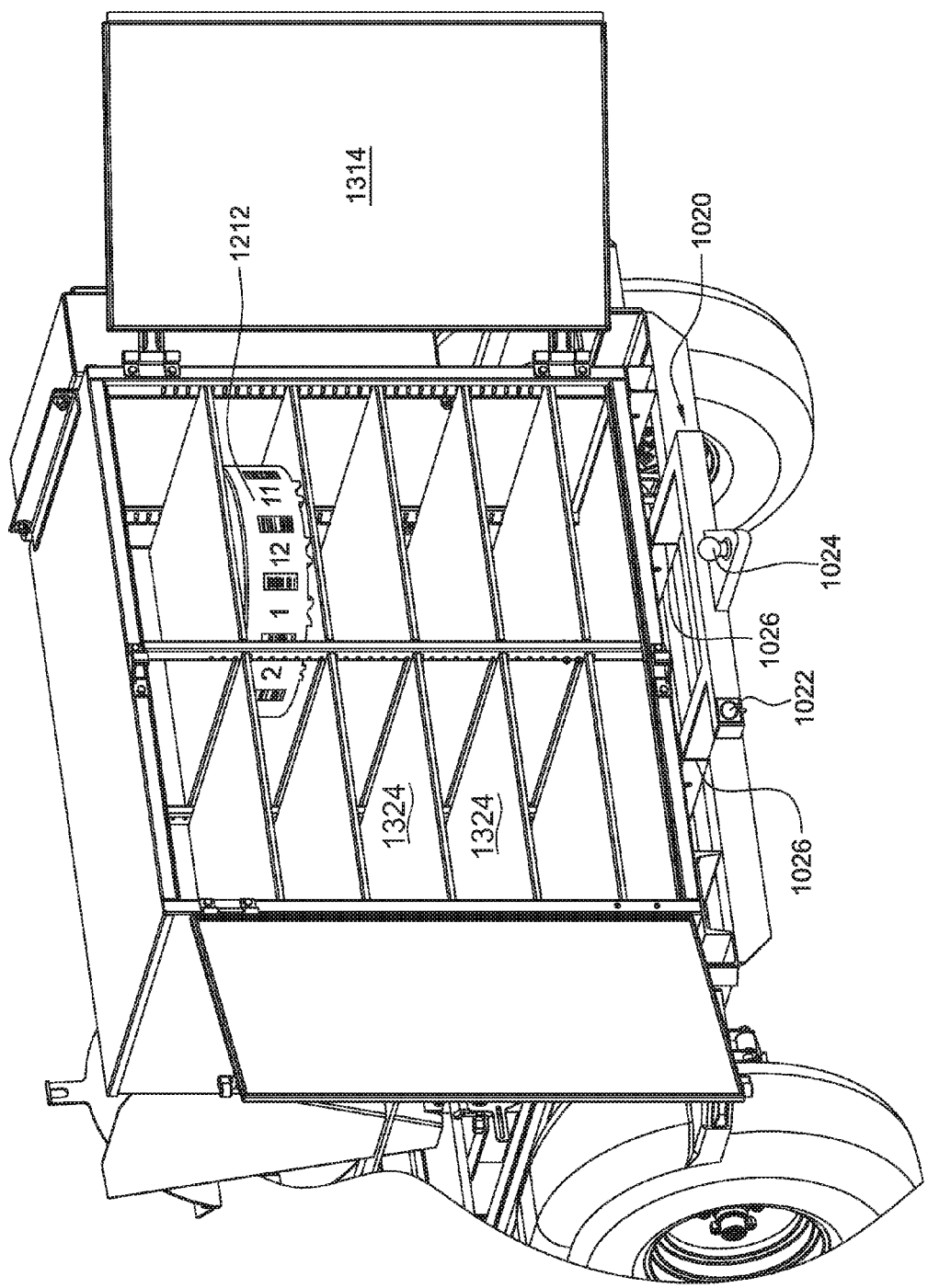
FIG. 8A is a rear elevational, schematic view of a storage cabinet showing doors open.
Figure 8B:
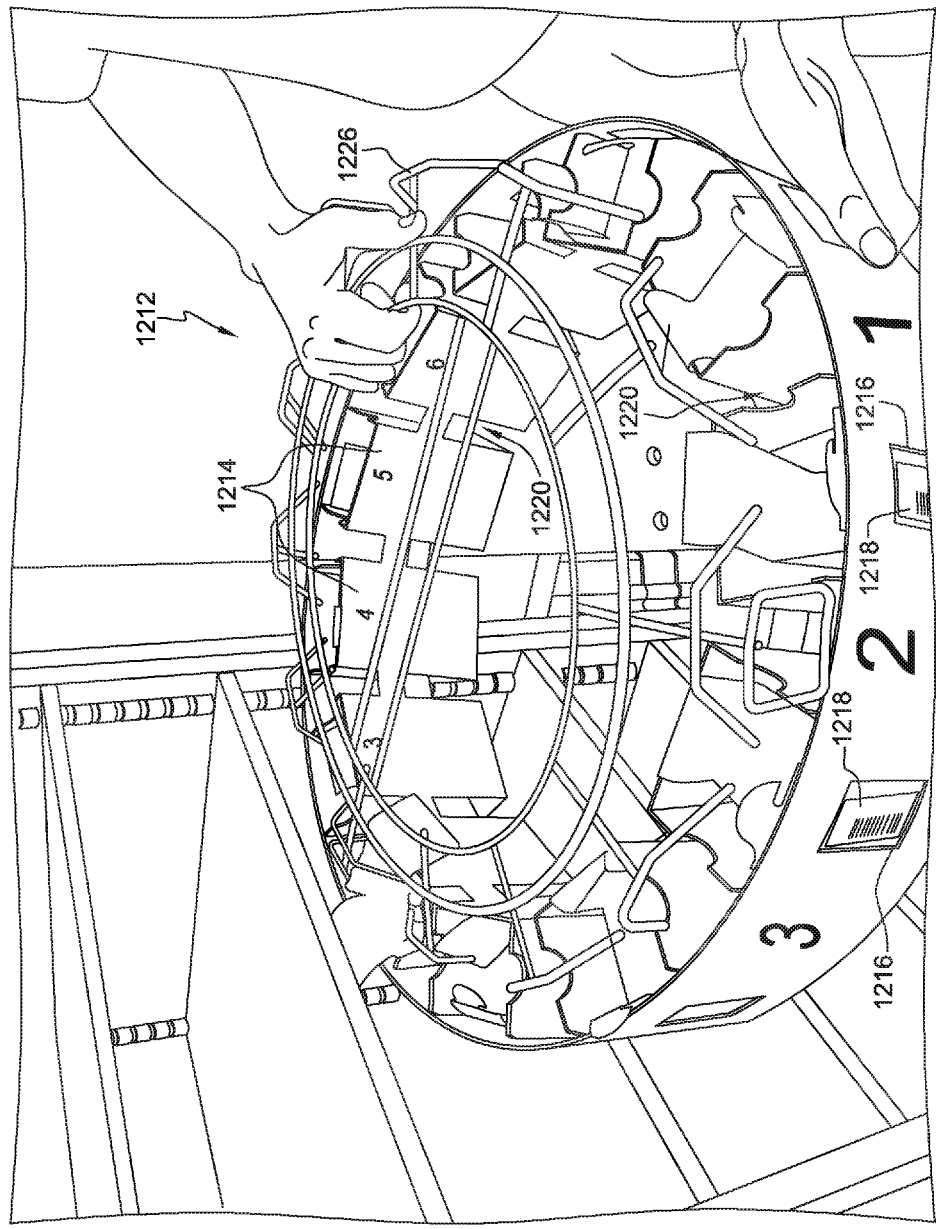
FIG. 8B is a perspective, schematic view of a sample collection tray being removed from the storage cabinet prior to its installation in the soil sampler.

Referring now also to FIG. 8A, there is shown a rear elevational, schematic view of an interior region of storage cabinet 1300.

A number of shelves 1324 are sized and configured to hold sample collection trays 1212.

Also visible in FIG. 8A is a removable auxiliary trailer hitch 1020. Hitch 1020 is received in hitch receivers 1026 that form part of the frame of trailer 1002. Hitch 1020 allows an auxiliary trailer or other similar device to be tandem connected to the rear of soil sampler 1000.

An electrical connector 1022 provides power, brake and turn signal connections from the vehicle rowing soil sampler 1000 to the auxiliary trailer, not shown, attached to hitch 1006 of soil sampler 1000.

An interchangeable ball 1024 allows connecting a wide variety of auxiliary trailers or similar equipment to removable auxiliary trailer hitch 1020.

The most prominent feature of soil sampler 1000 is a large collection drum 1102 having a rotational axis perpendicular to a major axis of trailer 1002.

Figure 2:
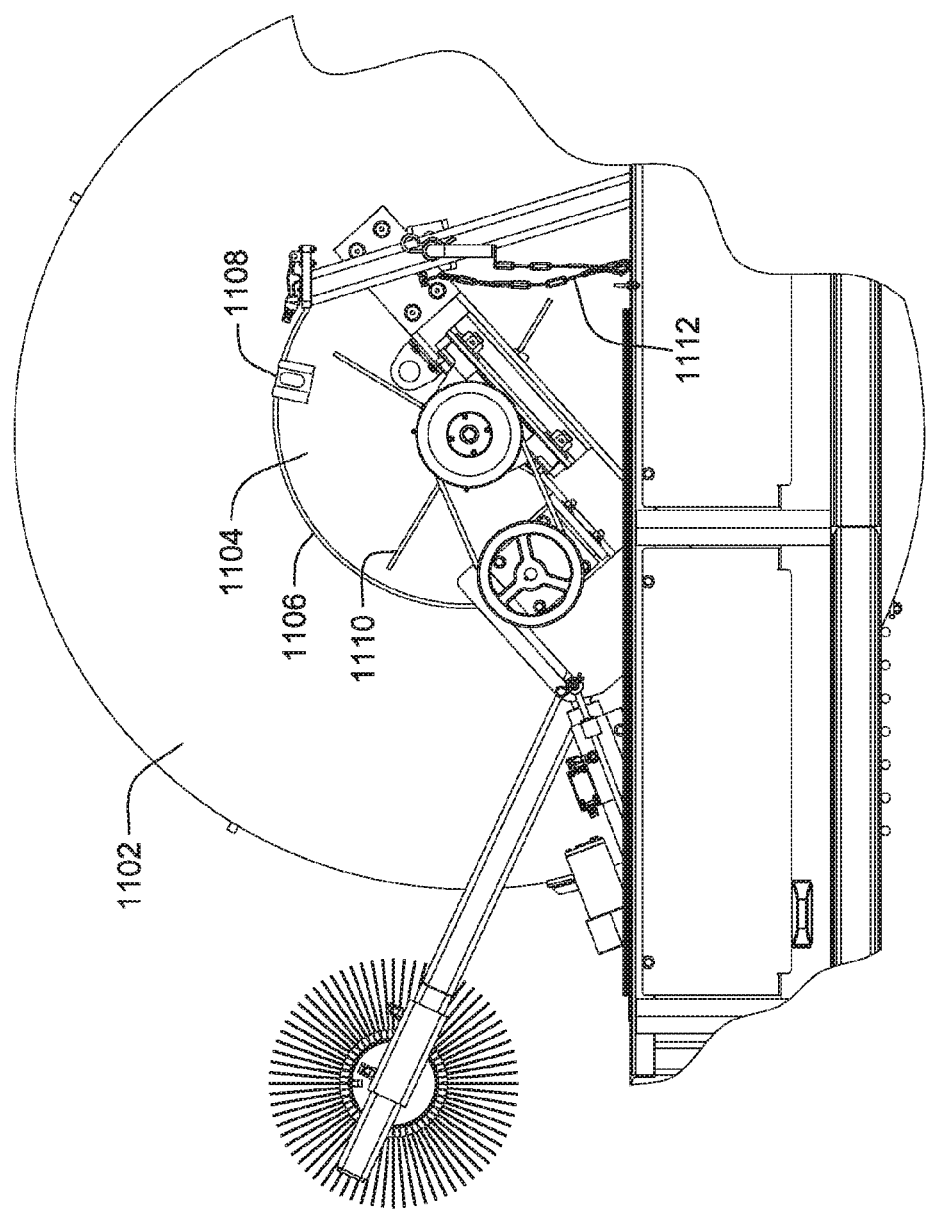
FIG. 2 is a right side elevational, schematic view of a portion of the collection drum and support mechanism therefor forming part of the soil sampler for FIGS. 1A and 1B.

Referring now to FIG. 2, there is shown a left side elevational, schematic view of a portion of collection drum 1102 and support mechanism therefor.

Figure 7:
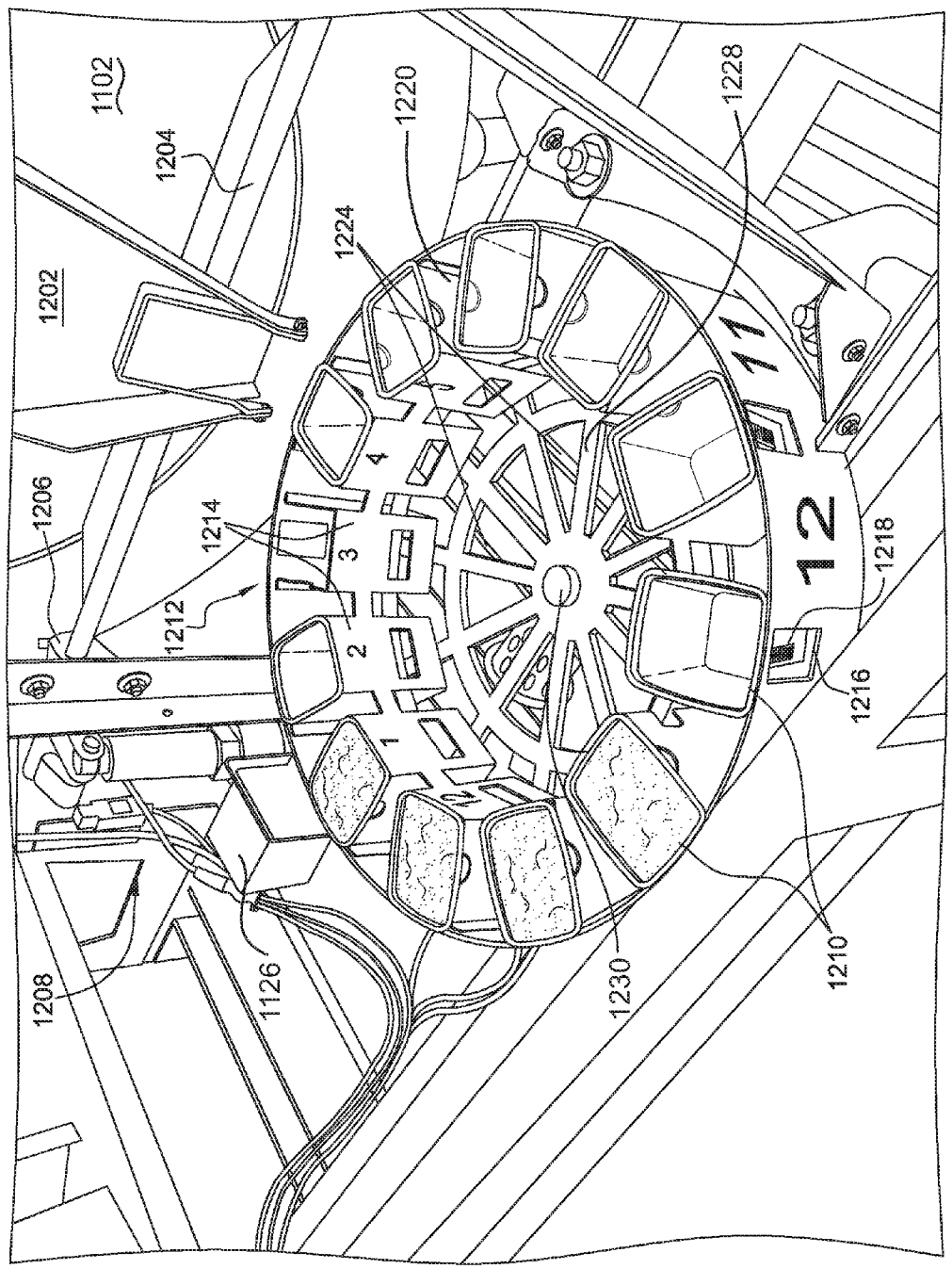
FIG. 7 is a right side elevational, schematic view of a portion of soil sampler showing a sample collection tray in a normal operating position.

Sample collection drum 1102 is typically made from a stainless steel alloy typically by a spinning process. The drum is typically formed in two individual halves that are assembled to the other by welding. A hole 1199, best seen in FIG. 7, is cut in the inboard (i.e., right) side of sample collection drum 1102. The circular piece of stainless steel, not specifically identified, is removed and used to provide material for a concentric reinforced support area 1104 welded to a center of the outboard (i.e., left) surface of sample collection drum 1102. Circumferential weld 1106 used to attach the concentric reinforced support area 1104 to sample collection drum 1102.

A securing bracket 1108 is welded to concentric reinforced support area 1104 near the outer perimeter thereof. Securing bracket 1108 is selectively attached to a securing chain 1112 so that collection drum 1102 may be kept from rotation during transportation of soil sampler 1000.

Buttresses or stiffeners 1110 radiate from the center of drum 1102 and concentric reinforced support area 1104 and are welded thereto.

Optionally, the interior of sample collection drum 1102 may be coated with a non-stick polymer, typically a polytetrafluoroethylene (PTFE), e.g., Teflon®. The same or a similar material may also be used to coat the upper surface of the sample extraction funnel 1202, best seen in FIG. 6.

Several things will be recognized by those of skill in the art. First, sample collection drum 1102 may be formed using techniques other than spinning. Also, materials other than polytetrafluoroethylene (PTFE) may be used for an anterior coating for the sample collection drum 1102 and/or sample extraction funnel 1202. Consequently, the invention is not considered limited to any particular drum manufacturing technique or optional coating material.

Referring now also to FIG. 3, there is shown a more detailed left side elevational, schematic view of sample collection drum 1102 and the support mechanism therefor.

A first pair of pillow blocks 1116 rotatively support drum axle 1118 that has a distal end, not specifically identified, fixedly attached to a center, not specifically identified, of concentric reinforced support area 1104. Bearings, not specifically identified, in pillow blocks 1116 allow drum axle 1118 and attached sample collection drum 1102 to rotate freely.

A first drive pulley 1120 is affixed to a proximal end, not specifically identified of drum axle 1118. A second drive pulley 1122 is attached to a shaft 1126 of a motor 1124, not visible in FIG. 3. In the embodiment chosen for purposed of disclosure, motor 1124 is an electric motor. It will be recognized by those of skill in the art that a hydraulic or pneumatic motor could be substituted therefor. Consequently, the invention is not considered limited to the electric motor chosen for purposes of disclosure. Rather, the invention is intended to include any suitable motor.

A drive belt 1128 couples first drive pulley 1120 and second drive pulley 1122. Drive belt 1128 is typically a conventional V-belt. It will also be recognized that "poly-V" or cog belts could likewise be substituted for V-belt 1128 with suitable modification to drive pulleys 1120 and 1122. Motor 1124 is provided with a tensioning mechanism adapted to compensate for stretching of V-belt 1128.

Pillow blocks 1116 and motor 1124 are both attached to a raiseable drum support arm 1130.

Figure 4A:
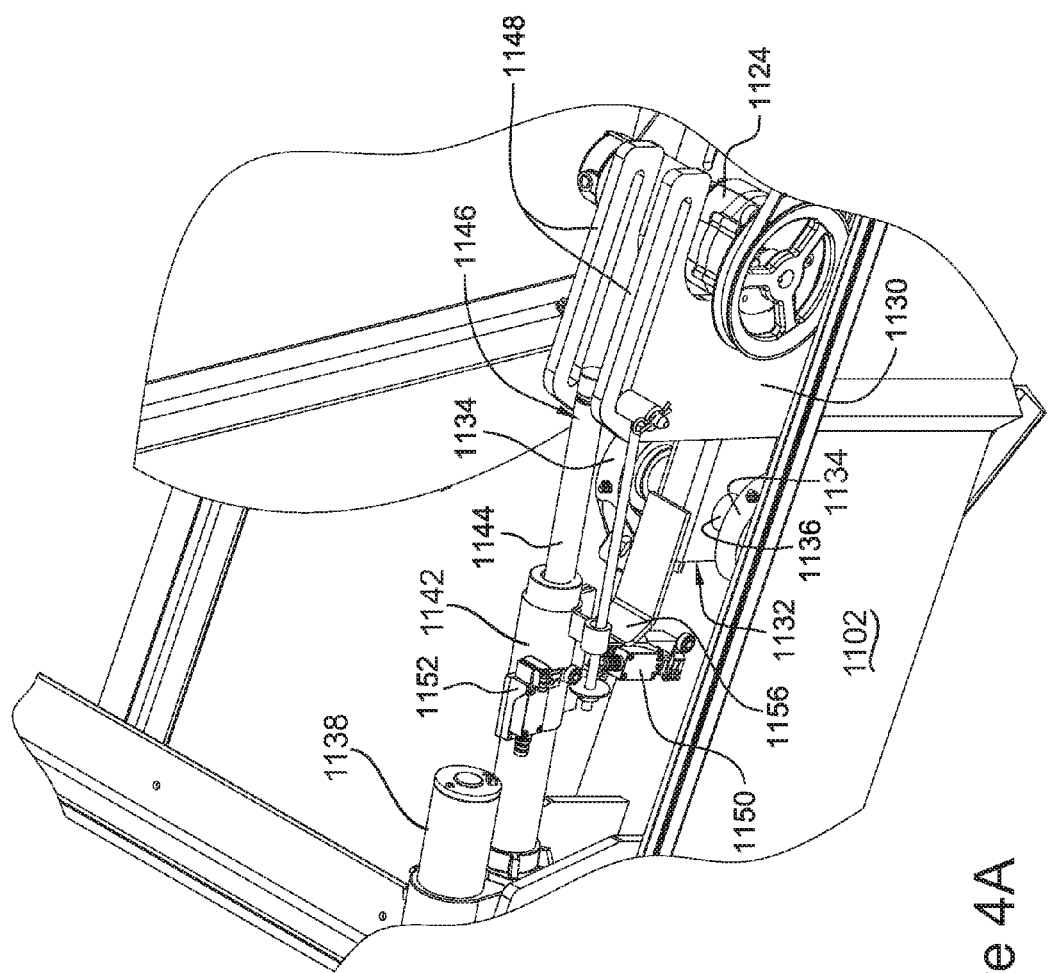
FIGS. 4A and 4B are detailed left side elevational views of the left end of a drum lift arm in a lowered and raised orientation, respectively.
Figure 4B:
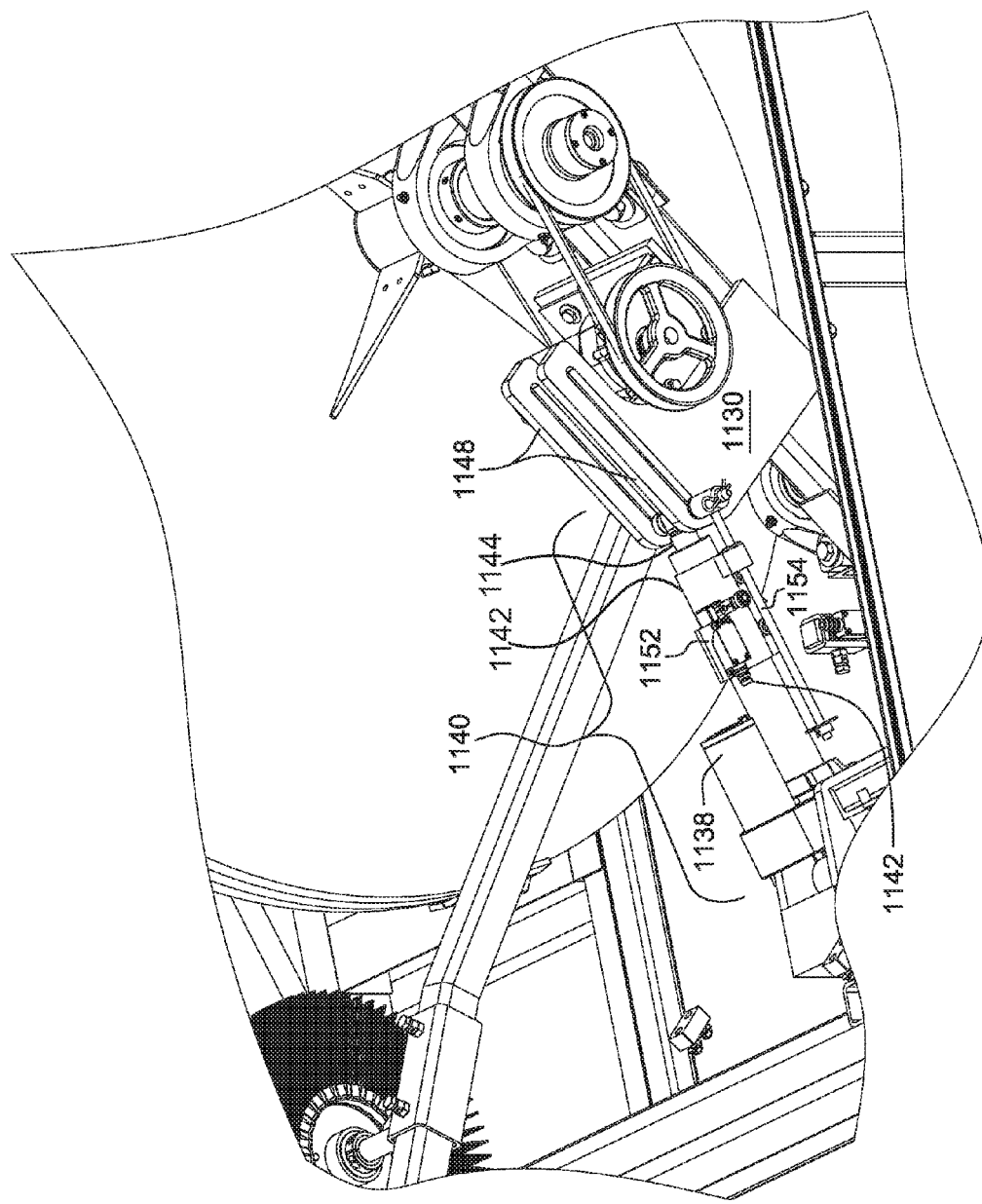

Referring now also to FIGS. 4A and 4B, there are shown detailed left side elevational views of the left end of raiseable drum support arm 1130 in a lowered and raised orientation, respectively. A proximal end 1132 raiseable drum support arm 1130 is rotatively attached to trailer frame 1102 through a second pair of pillow blocks 1134 and a drum lift arm axle 1136.

A drum support arm lift arm motor 1138 drives a cylinder 1142 with a piston 1144 through a drive mechanism 1134. As seen in FIG. 4B, piston 1144 is completely withdrawn into cylinder 1142 causing the raiseable drum support arm 1130 to be in a raised position. However, in FIG. 4A, piston 1144 is fully extended causing raiseable drum support arm 1130 to be in a lowered position. Note that soil sampling by soil sampler 1000 is accomplished with drum lift arm 1130 in a lowered position. In the embodiment chosen for purposes of disclosure, raiseable drum support arm 1130 drum support arm lift motor 1138 is an electric motor that cooperates with a gear drive mechanism, not specifically identified, to cause a worm gear, not shown, to extend and retract piston 1144 from and into cylinder 1142. It will be recognized that drum support arm lift motor tor 1138, drive mechanism 1140 and cylinder 1142 could be replaced by hydraulic or pneumatic cylinders believed to be well known to those of skill in the art. Consequently, the invention is not considered limited to the electric drum support arm lift motor r 1138, drive mechanism 1140 and cylinder 1142. Rather, the invention is intended to include any and all suitable replacement mechanisms and/or devices.

A distal end 1146 of piston 1144 is attached to a pair of slotted plates 1148 attached to raiseable drum support arm 1130. Upper and lower limit switches 1150, 1152 limit the travel of piston 1144 in the lowered and raised positions respectively, of raiseable drum support arm 1130. Lower limit switch 1150 is actuated by a control rod 1154 operatively attached to distal end 1146 of piston 1144. Upper limit switch 1150 is actuated by a switch actuation tab 1156 attached to proximal end 1132 of raiseable drum support arm 1130.

A hinged cover 1184, best seen in FIGS. 1A and 1B, covers the drum lift mechanism, not specifically identified. Hinged cover 1184 provides protection to the lift mechanism from weather and airborne debris during transport and operation of soil sampler 1000. A hinge 1186 and a front edge of hinged cover 1184 pivotally attached hinged cover 1184 to trailer 1102. A latch 1188, best seen in FIG. 5C, secures the rear edge of hinged cover 1184.

In operation, providing electrical power to drum support arm lift motor 1138 causes rotation it to rotate and, consequently, transmit rotary motion to a gearbox, not specifically identified to a helical screw drive, not specifically identified, within cylinder 1142. Depending upon the direction of rotation of drum support arm lift motor 1138, piston 1144 is either extended from or withdrawn into cylinder 1142. If raiseable drum support arm 1130 is in a lowered position (FIG. 4A), piston 1144 is extended from within cylinder 1142. Drawing piston 1144 into cylinder 1142 causes raiseable drum support arm 1130 to rotate on drum support axle 1136 supported in pillow blocks 1134, thereby raising sample collection drum 1102. Sample collection drum 1102 supported on raiseable drum support arm 1130 is lowered by extending piston 1144 from cylinder 1142, thereby allowing raiseable drum support arm 1130 to return to is lowered position. It should be noted that the lower position of raiseable drum support arm 1130 and sample collecting drum 1102 is the operative position. Sampling drum 1102 may be raised for travel.

Slots, not specifically identified in the pair of slotted plates 1148 allow the distal end 1146 of piston 1144 to move in response to bumping or jolting of soil sampler 1000. Such bumping or jolting may occur while sampling rough terrain or when transporting soil sampler 1000 between sampling locations.

Figure 5A:
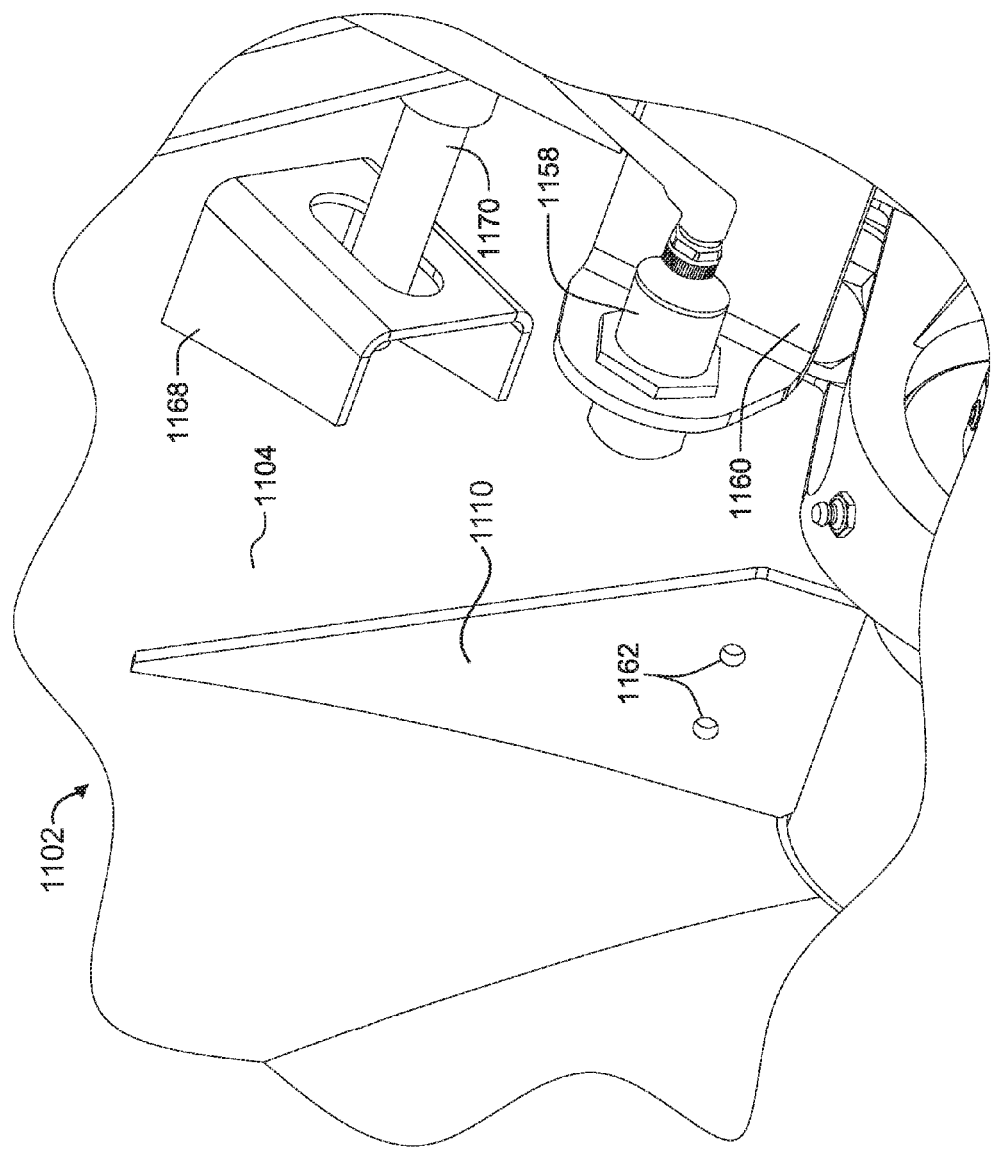
FIG. 5A is a detailed left perspective view of a portion of the sample collection drum and an anti-rotational device therefor.
Figure 5B:
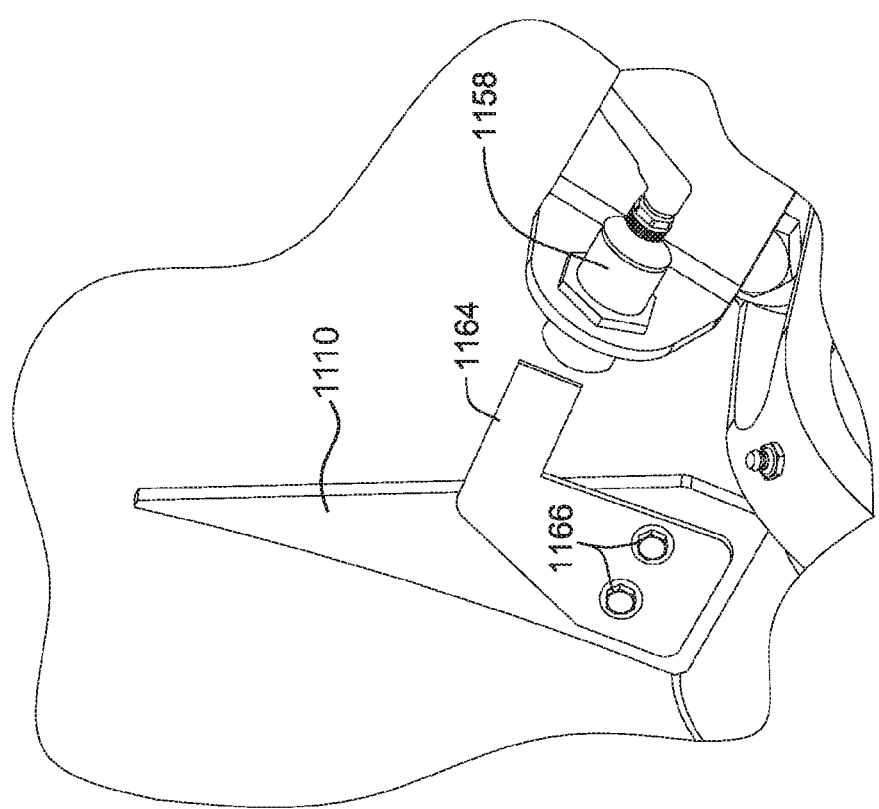
FIG. 5B is a detailed left perspective, schematic view of a portion of the sample collection drum showing a proximity rotational sensor and a flag for activating the proximity sensor.

Referring now also to FIGS. 5A and 5B, there are shown a perspective, schematic view of a portion of sample collection drum 1102 and a proximity sensor 1158 and a detailed view of proximity sensor 1158 and a stiffener 1110, respectively. In FIG. 5A a proximity sensor 1158 is affixed to a bracket 1160 that is, in turn attached to raiseable drum support 1130. Note that raiseable drum support arm 1130 is not visible in FIG. 5A. Stiffener 1110 has a pair of holes 1162 that allows attachment of a flag 1164 using bolts 1166.

Proximity sensor 1158 is typically a magnetic sensor that creates an output signal, not shown, as a ferromagnetic material passes within a predetermined range thereof. As seen in FIG. 5B, flag 1164 passes by proximity sensor 1158 as sample collection drum 1102 rotates. In the embodiment chosen for purposes of disclosure, a flag 1164 is attached to a single one of stiffeners 1110. This allows a proximity sensor 1158 output signal once per revolution of sample collection drum 1102.

It will be recognized that additional flags 1164, not shown, may be attached to one, two or three additional ones of stiffeners 1110 to generate proximity sensor 1158 output signal twice, three times or four times per revolution of sample collection drum 1102, respectively to meet the need of an alternate operating environment or circumstance. It will be further recognized that alternate sample collection drum 1102 rotation sensing devices or methods may be substituted for the magnetic proximity detection technology used for purposes of disclosure. Alternate technologies may use reflective "dots" or patches applied to the exterior surface of sample collection drum 1102 at appropriate intervals in conjunction with a photo-reflective sensor system using a visible light source, a laser, or some alternate light source and a photo detector compatible with the chosen light source. Consequently, the invention is not considered limited to the ferromagnetic proximity sensing system used for purposes of disclosure. Rather, any suitable alternate sample collection drum rotation measurement system is intended to be in the claimed invention.

As seen in FIG. 5A, an anti-rotation bracket 1168 is welded to concentric reinforced support area 1104 of sample collection drum 1102. An anti-rotation pin 1170 may be secured in anti-rotation bracket 1168 that, when secured, prevents sample collection drum 1102 from rotating. Sample collection drum 1102 is typically secured for transporting soil sampler 1000.

Figure 5C:
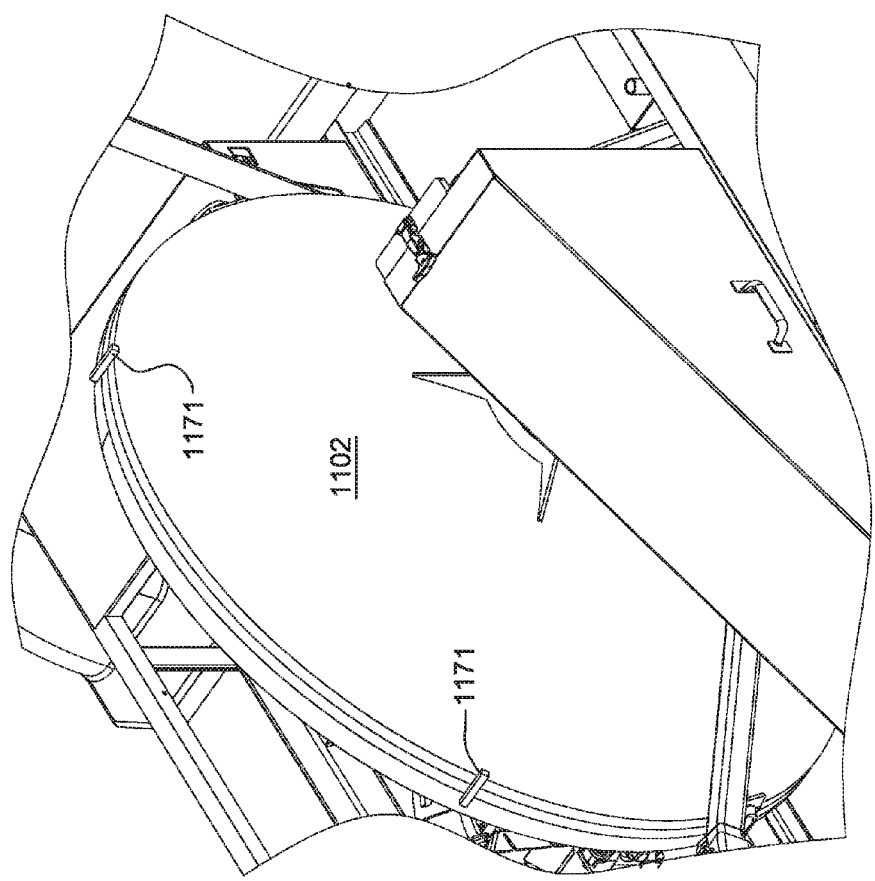
FIG. 5C is a front left perspective view of the sample collection drum showing a probe attachment ring.

Referring now also to FIG. 5C, there is shown a front perspective, schematic view of an exterior surface of sample collection drum 1102. One or more ground-engaging cleats 1171 may be attached to a perimeter edge of sample collection drum 1102. Ground engaging cleat(s) 1171 help keep sample collection drum 1102 rotating when traversing uneven terrain.

Also seen in FIG. 5C is a more detailed view of hinged cover 1184 and a locking mechanism 1188 for securing hinged cover 1184 in a closed position.

Referring now also to FIG. 6A-1-6A-3, there are shown side perspective, schematic views of representative examples of three interchangeable sampling probes 1174a, 1174b, 1174c. Sampling probes 1174a-1174c are representative of numerous possible variations in interchangeable sampling probes and designations 1174a-1174c are intended to represent all possible sampling probes that may be referred to generically as 1174n, not specifically shown.

Sampling probes 1174a, 1174b . . . 1174c and associated tips 1176a, 1176b, 1176c may have one of several different inside diameters. Typical probes have nominal diameters in the range of 0.75 or 1.00 inches. It will be recognized that probes and/or tips other inside diameters may be provided to meet a particular operating circumstance or environment. Therefore, the invention is not considered limited to inside diameters of in the range of 0.75 or 1.00 inches.

Sampling probes 1174a, 1174b . . . 1174c are each substantially conical with their largest diameter being at their lower, distal ends. Internal surfaces of probes 1174a, 1174b . . . 1174c may be smoothly tapered with a substantially uniform wall thickness, not specifically identified, or, in alternate embodiments, may have a step or chamfer on an inside surface, not specifically identified, to facilitate release of a sampled of Sampling probes 1174a, 1174b . . . 1174c each have a body portion 1175a, 1175b . . . 1175c and a replaceable tip portion 1176a, 1176b . . . 1176c screwably attached to body portion 1175a, 1175b . . . 1175c.

A pair of diametrically opposed "flats" 1182 are disposed adjacent a lower edge of tip portions 1176a, 1176b . . . 1176c. A similar pair of diametrically opposed "flats" 1178 is disposed adjacent lower, distal ends of body portions 1175a, 1175b . . . 1175c. Flats 1178 and 11781182 allow gripping respective body portions 1175a, 1175b . . . 1175c and tip portions 1176a, 1176b . . . 1176c with a tool, for example an open-end wrench or the like for securely attaching a tip portion 1176a, 1176b . . . 1176c to a body portion 1175a, 1175b . . . 1175c or attaching to a body portion 1175a, 1175b . . . 1175c to a probe attachment ring 1172 (best seen in FIG. 6C) on the sample collection drum 1102.

Optionally, sampling probes 1174a, 1174b . . . 1174c may have a coating, not shown, of a polymer such as polytetrafluoroethylene (e.g., Teflon®) or similar polymer to create a low friction "non-stick" surface on the inside surface, not specifically identified, of sampling probes 1174a, 1174b . . . 1174c and tip portions 1176a, 1176b . . . 1176c. In still other embodiments, a similar low friction "non-stick" material may be applied to an outside surface, not specifically identified of sampling probes 1174a, 1174b . . . 1174c and/or tip portions 1176a, 1176b . . . 1176c.

Sampling probes 1174a, 1174b . . . 1174c have threads 1180 at a lower end thereof. Threads 1180 are sized and configured to screwably engage a probe attachment ring 1172 on an outer perimeter of sample collection drum 1102.

Figure 6B:
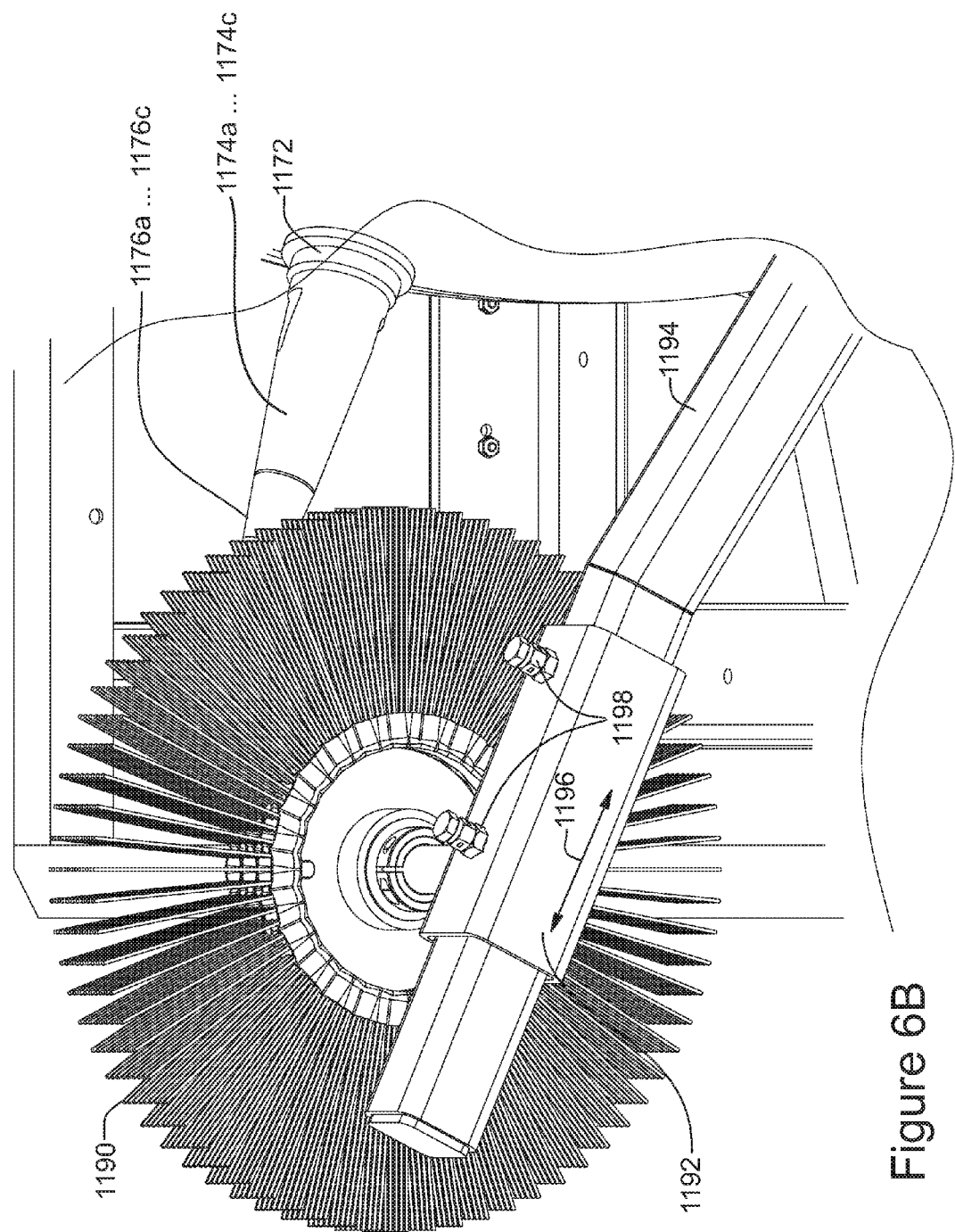
FIG. 6B is a left side perspective view of a sampling probe interacting with a probe tip cleaning brush.

Referring now also to FIG. 6B, there is shown a side perspective, schematic view of a portion of the outer edge of sample collection drum 1102. A sampling probe 1176a, 1176b . . . 1176c having a respective tip 1176c (represented by 1176a, 1176b . . . 1176c) is shown attached to sample collection drum by a probe attachment ring 1172.

A tip cleaning brush 1190 is rotatively attached to a sliding sleeve 1192 that slides bi-directionally along a distal end of brush support 1194 in directions shown by arrow 1196. Tip cleaning brush 1190 is thereby positioned to engage at least a tip portion 1176a, 1176b . . . 1176c as sample collection drum 1102 rotates. Tip cleaning brush 1190 may be adjusted to engage tip 1176a, 1176b, . . . 1176c of sampling probe 1174a, 1174b . . . 1174c of varying lengths by moving sliding support 1192 in the direction indicated by arrow 1196 to a desired position and then tightening sleeve holding screws 1198 to secure sliding support 1192 to a fixed member 1194.

Sampling probes 1174a, 1174b . . . 1174c are screwably attached and retained on the perimeter, not specifically identified, of sample collection drum 1102 of a probe attachment ring 1172 welded or otherwise attached to the perimeter of sample collection drum 1102. Probe attachment ring 1172 has internal threads, not shown, to engage external threads 1180 of a selected one of sampling probes 1174a, 1174b . . . 1174c. Probe attachment ring 1172 surrounds an opening, not shown, in sample collection drum 1102 allowing communication between a hollow interior, not shown, of a selected one of sampling probe 1174a, 1174b . . . 1174c and the interior, not specifically identified, of sample collection drum 1102.

While the operation of soil sampler 1000 is discussed in more detail hereinbelow, a brief explanation of the sampling process helps to understand the function of sample collection drum 1102 and sample probes 1174a, 1174b . . . 1174c A sample probe 1174a, 1174b . . . 1174c is attached to probe attachment ring 1172 of sample collection drum 1102. A tow vehicle, not shown and forming no part of the present invention, pulls soil sampler 1000 across an area from which soil samples are to be taken. As sample collection drum 1102 rotates, an attached one of sample probes 1174a, 1174b . . . 1174c penetrates the soil and captures a "core sample" of the soil. The depth of the core sample is determined primarily by the length of sampling probe 1174a, 1174b . . . 1174c selected. The sample collection drum 1102 continues to rotate, as sample probe 1174a, 1174b . . . 1174c becomes inverted and gravity acting on the core sample in the inverted conical sampling probe 1174a, 1174b . . . 1174c causes the sample to fall into sample collection drum 1102. The non-stick coating, not shown, applied to the interior of sampling probes 1174a, 1174b . . . 1174c aid gravity in this process. The process continues until either a predetermined number of samples have been collected or, alternately, a predetermined area has been sampled.

Referring now also to FIGS. 7 and 8B, FIG. 7 there are shown a right side elevational, schematic views of a portion of soil sampler 1000. In FIG. 8B, sample collection tray 1212 is shown being removed from storage cabinet 1300 prior to its installation in soil sampler 1000. In FIG. 7, a sample collection tray 1212 is shown in a normal operating position in soil sampler 1000.

As may be seen in FIG. 1A, the right side of sample collection drum 1102 is largely open. An interior surface, not specifically identified, of sample collection drum 1102 has one or more mixing blades, not visible in FIG. 7, disposed parallel to the axis of rotation of sample collection drum 1102. Similar blades may be seen in cement mixers and other such types of equipment. Therefore, such mixing blades are believed to be well known to those of skill in the art and, consequently, are not further discussed herein. The mixing blades blend the individual samples introduced into sample collection drum 1102 from the sampling probe 1174a, 1174b . . . 1174c. After all samples have been collected, rotation of sample collection drum 1102, effected by drum drive motor 1124, continues for a duration long enough to thoroughly mix the collected samples.

A sample extraction funnel 1202 is mounted to a rotatable shaft 1204 supported in a pair of pillow blocks 1206, only one visible in FIG. 7. Sample extraction funnel 1202 may be selectively rotated by an actuation mechanism 1208 to allow extraction funnel 1202 to be rotated into an interior region, not specifically identified, of sample collection drum 1102. When so inserted, all sample contents within sample collection drum 1102 eventually fall onto an upper surface, not specifically identified, of sample extraction funnel 1202 and, subsequently, into a collection container 1210.

An actuation mechanism 1208 is operatively connected to sample extraction funnel 1202 via rotatable shaft 1204. Actuation mechanism 1208, upon application of a signal, selectively rotates sample extraction funnel 1202 between a position within sample collection drum 1102 (an operating position) and alternately, a position outside sample collection drum 1102 (an inoperative position).

A circular sample collection tray 1212, shown in more detail in FIG. 8B, contains 12 container compartments 1214 adapted to support sample containers 1210 that are typically closable cardboard boxes, plastic containers with detachable lids, sealable paper sacks or the like, none forming part of the present invention.

Circular sample collection tray 1212 has windows 1216 disposed in an outside perimeter wall that allows machine-readable (e.g., bar coded, etc.) labels 1218 appropriately placed on sample containers 1210 to be visible for scanning. Bar coded labels 1218 form no part of the present invention. It will be recognized that other machine readable labels may be substituted for bar coded labels. As stated neither sample containers 1210 nor machine-readable labels 1218 form any part of the present invention but are included to illustrate the functionality of the novel soil sampler 1000.

Container compartments 1214 are separated by open spaces 1220 that allow any excessive collected sample in sample collection drum 1102 to fall through open spaces 1220 when the sample is discharged from sample collection drum by sample extraction funnel 1202.

A wire container hold down member 1226 may be placed on top of sample collection tray 1212 to hold sample containers 1210 in place in sample container compartments 1214. More importantly, wire container hold down member 1226 holds sample containers 1210 open to receive samples from sample collection drum 1102.

Figure 9:
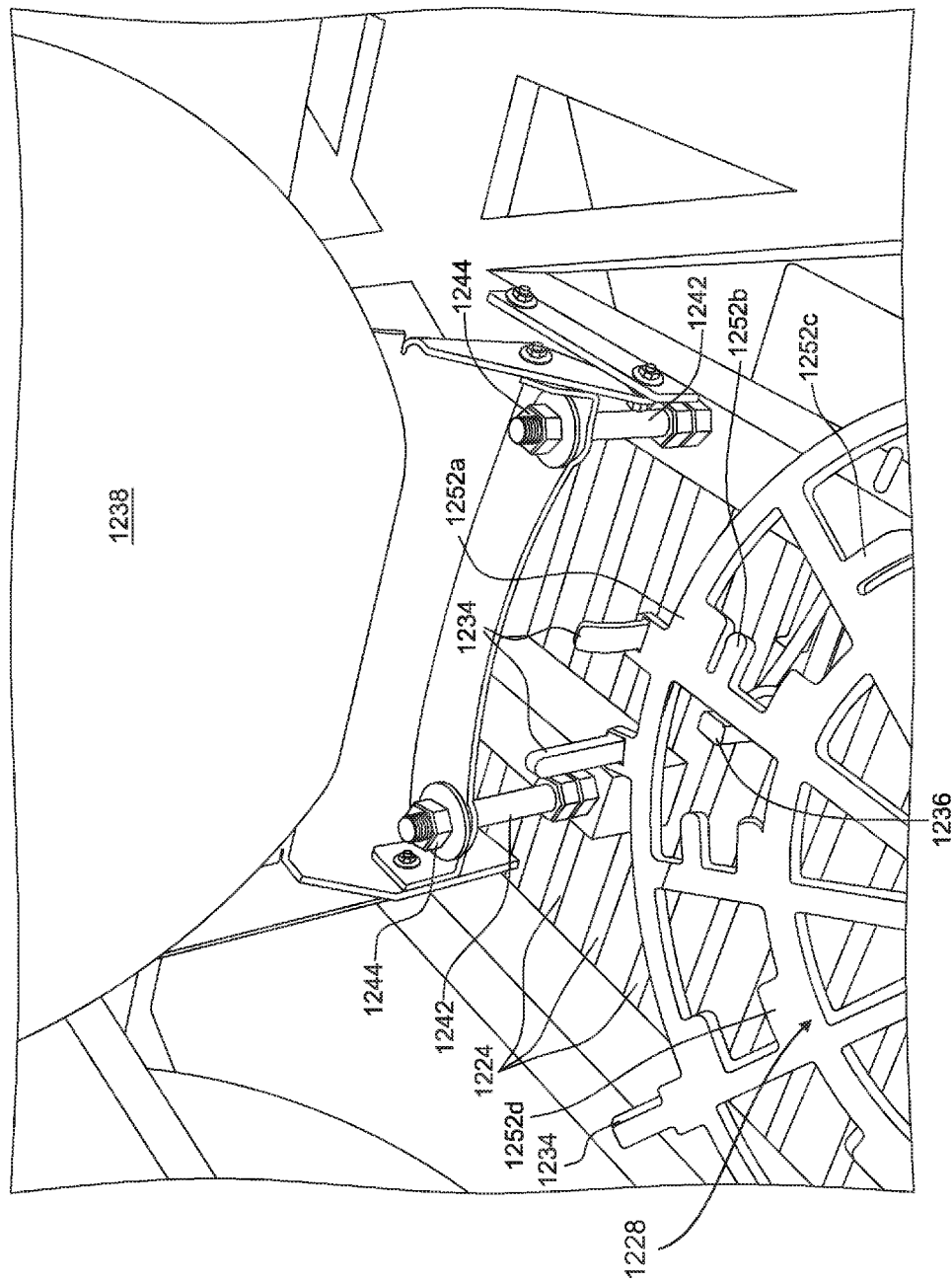
FIG. 9 is a right perspective, schematic view of a portion of a sample collection carousel of the soil sampler.

Referring now also to FIG. 9, there is shown a right perspective, schematic view of a portion of sample collection region of soil sampler 1000.

A collection assembly carousel platform 1228 is disposed substantially horizontally above parallel frame members 1224 forming part of the frame, not specifically identified, of trailer 1002. This construction allows excess sampled material to fall through to the ground between parallel frame members 1224 while providing good protection of the mechanism thereby preventing damage from objects protruding upward from the ground while soil sampler 1000 traverses rough terrain.

Collection assembly carousel platform 1228 rotates on an axle 1230, best seen in FIG. 7. An actuator below and to the left of carousel platform 1228, not visible in FIGS. 7-9, provides on command a predetermined rotation to the sample collection carousel platform 1228. In the embodiment chosen for purposes of disclosure, collection carousel platform 1228 has 12 sample container compartments 1214. Consequently, to advance collection assembly carousel platform one sample compartment 1214, a rotation of 30° must be applied. It will be recognized by those of skill in the art that collection assembly carousel platform may be designed and implemented to support sample collection trays having other than 12 compartments and that the actuation mechanism must be modified for a corresponding amount of rotation. Consequently, the invention is not considered limited to collection assembly carousel platforms and sample collection trays having 12 compartments.

Upright members 1234 spaced around the perimeter of carousel platform 1228 center sample collection tray 1212 thereupon. It should be noted that sample collection tray 1212 may only be placed on collection assembly carousel platform 1228 in only one angular orientation.

A first detent (i.e., anti-rotation) mechanism 1236 allows collection assembly carousel platform 1228 to rotate counter-clockwise as viewed from above but prevents collection assembly carousel platform 1228 from moving in a clockwise direction. A second detent mechanism, not visible in FIG. 9, selectively prevents/allows collection assembly carousel platform 1228 from rotating counter-clockwise when collection assembly carousel platform 1228 is locked for receiving a sample.

Figure 10:
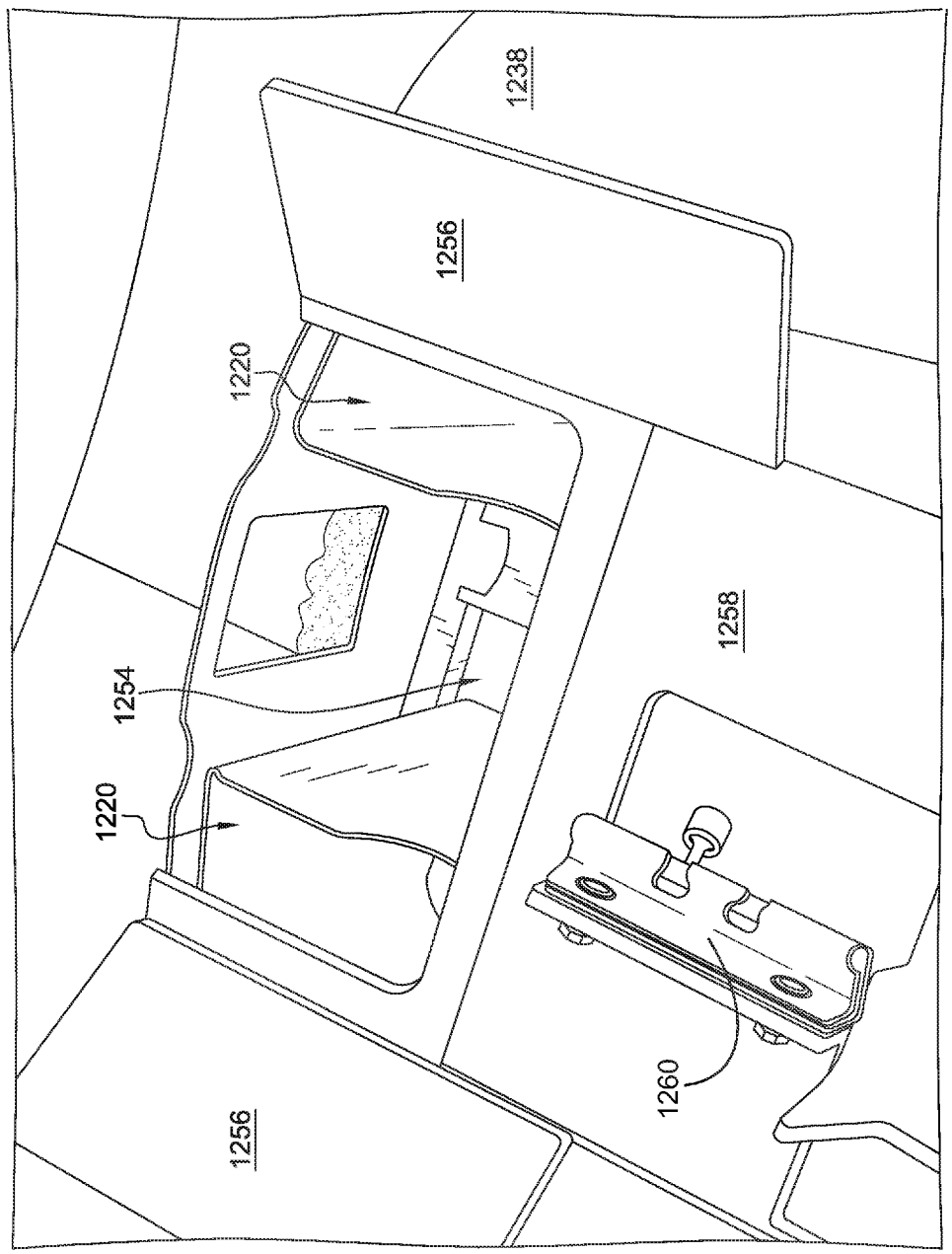
FIG. 10 is a detailed, partial, schematic view of a hinged cover showing an openable access hatch for loading samples into the carousel.

A hinged sample collection carousel cover 1238 is manually movable between an upright, open position as seen in FIG. 9, and a closed position whereat hinged cover 1238 is substantially horizontal and covering sample collection tray 1212. Hinged cover 1238 is supported on a pair of threaded rods 1242 and retained by height adjusting nuts 1244. This arrangement allows the height of hinged cover 1238 to be adjusted to allow for sample collection trays 1212 of different heights to be utilized to meet a particular operating circumstance or environment. As best seen in FIG. 10, hinged cover 1238 has an opening 1254 at an outer perimeter that allows sampled material from the sample extraction funnel 1202 to enter a sample container 1210. A pair of wings 1256 help guide sampled material through opening 1254. A sliding cover 1258 with a latch 1260 may be moved outwardly to cover opening 1254. Hinged cover 1238 thereby protects collected samples from loss, contamination, and/or damage.

Referring again also to FIG. 9, collection assembly carousel platform 1228 is typically formed from steel or another ferromagnetic material. The geometry of carousel platform 1228 includes a unique pattern in a region under each sample container compartment 1214. Four steel regions 1252a, 1252b, 1252c, 1252d are selectively provided at four different radii 1248a, 1248b, 1248c, 1248d (best seen in FIG. 11) to provide 24 unique combinations that may be used to identify the exact instantaneous angular position of collection assembly carousel platform 1228.

Figure 11:
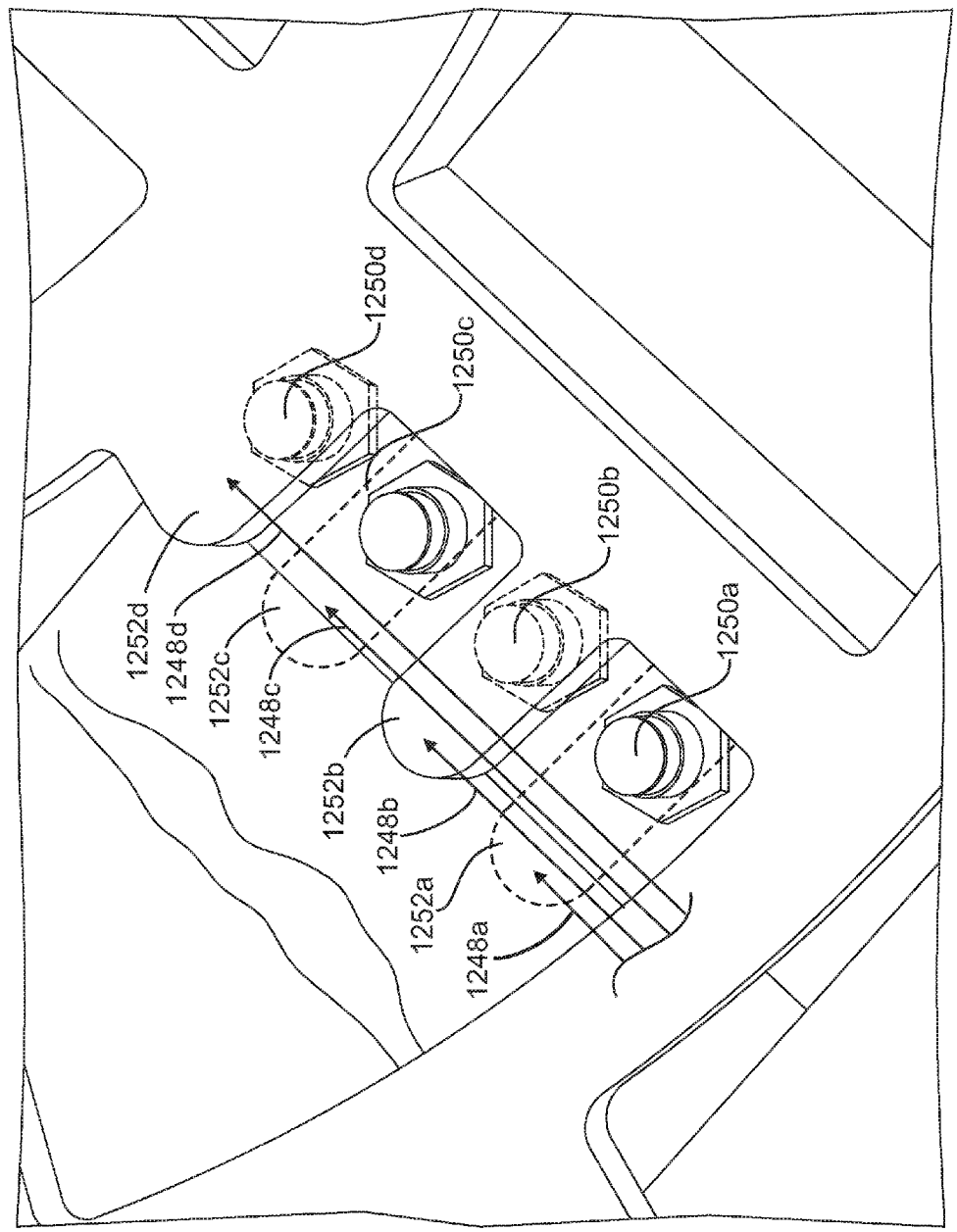
FIG. 11 is a detailed plan, schematic view of a portion of the sample carousel showing position sensors.

Referring now also to FIG. 11, there is shown a detailed, top plan, schematic view of a portion of sample collection carousel 1128. A series of four magnetic proximity sensors 1250a, 1250b, 1250c, 1250d are spaced apart and positioned to sense ferromagnetic structures (i.e., steel regions 1252a, 1252b, 1252c, 1252d) as they pass above their respective sensors 1250a, 1250b, 1250c, 1250d. Note that only regions 1250b and 1250d are present in FIG. 11. Regions 1250a and 1250c are shown in dashed lines. By selecting unique combinations of steel regions 1252a, 1252b, 1252c, 1252d theoretically allows 24 combinations to be sensed (i.e., the permutation of four things taken four at a time). In the disclosed embodiment, only 12 unique combinations are required. The sensed ferromagnetic structures are fingers or regions 1252a, 1252b, 1252c, 1252d. In FIG. 9, only fingers or regions 1252a, 1252b, 1252c are shown. This arrangement gives the electronic controller (i.e., primarily comprising touch screen display 1504, custom electronic controller board 1522, and general purpose computer 1524), best seen in FIG. 13 precise information regarding which of rotational position of collection assembly carousel platform 1228.

A hinged cover 1238 1202 normally in a lowered position over sample collection tray 1212 while collecting samples is raised to an upright position as seen in FIG. 9 in load and unload sample collection trays 1212 from collection assembly carousel 1228.

A bar code scanner assembly 1262, best seen in FIG. 7, is disposed and adapted to scan bar coded labels 1218 through openings windows 1216 in sample tray 1212.

Typically, sample containers 1210 have bar coded labels 1218 attached prior to sample containers 1210 being loaded into a sample collection tray 1212. It will be recognized that labels must be positioned at a location such that they are visible through windows 1216.

Prior to collecting samples, the bar codes of the sample containers 1210 in the sample collection tray 1212 are electronically loaded into controller 1502 and associated with each of sample container compartments 1214. Consequently, controller 1502 can cross check the position of collection assembly 1228 and ensure that an expected bar-coded collection container 1210 is where it is supposed to be.

In operation, first a sample collection tray 1212 with sample containers 1210 loaded in sample container compartments 1214 is loaded onto collection assembly carousel platform 1228. The desired number of soil samples has been collected in sample collection drum 1102, and then sample collection drum 1102 is rotated and sample extraction funnel 1202 is inserted into an opening in sample collection drum 1102. Mixed soil samples fall onto the upper surface of sample extraction funnel 1202 where they slide downward until they are discharged through opening 1254 in hinged carousel cover 1238 and guided by wings 1256 into a waiting sample container 1210 in a respective sample container compartment 1214.

Referring again also to FIG. 1A, a combined storage and electronics cabinet 1300 may be seen. An electronics enclosure 1302 protrudes from the right side of storage and electronics cabinet 1300.

Figure 12:
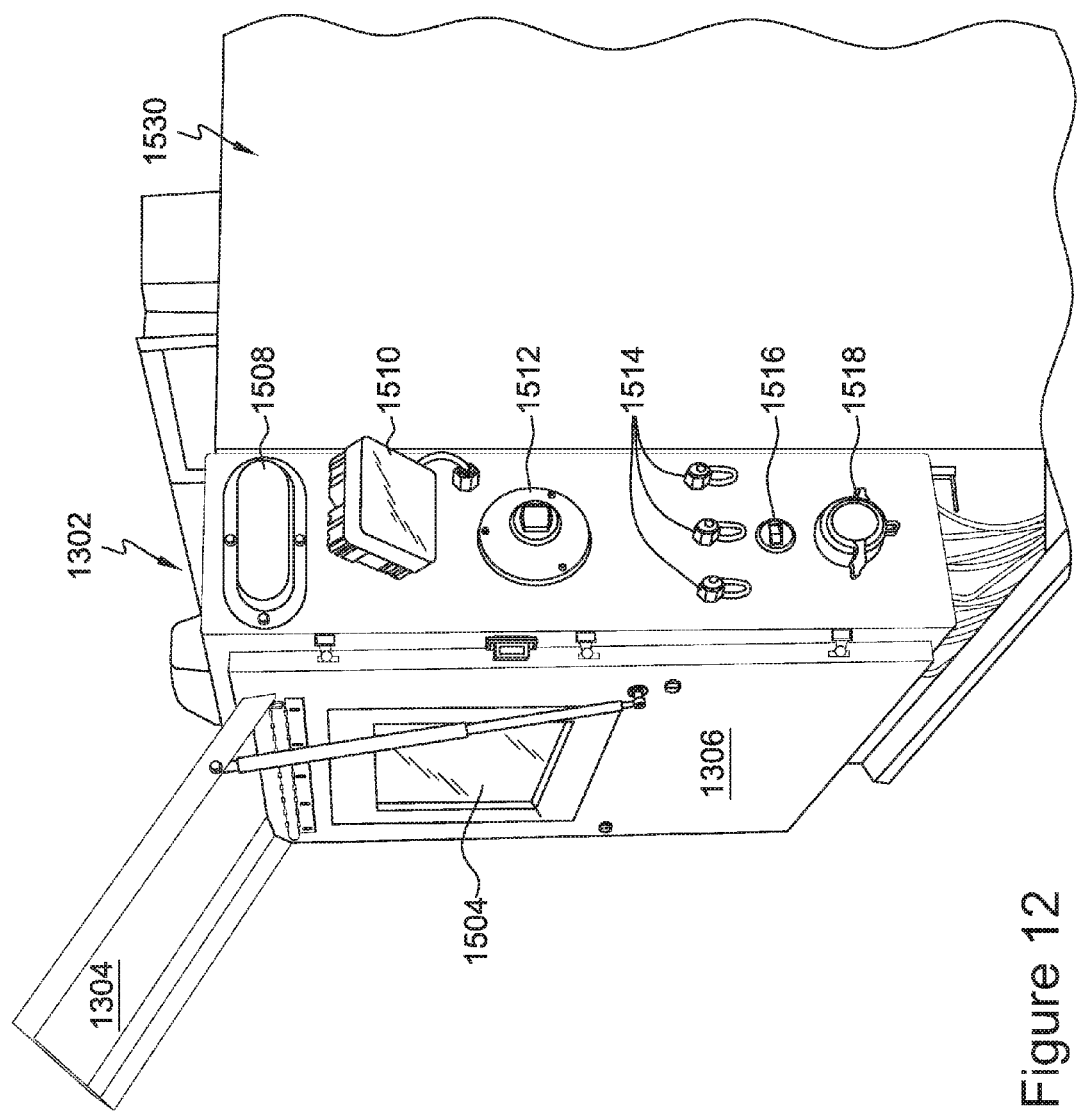
FIG. 12 is a side perspective, schematic view of a protruding electronics enclosure.

Referring now also to FIG. 12, there is shown a right side elevational, schematic view of electronics enclosure 1302. A weather tight access door 1304 on the right side of electronics enclosure may be raised to reveal a touch screen display 1504 mounted on an interior front panel 1306. Internal front panel may be opened further to revel an electronics compartment that contains electronic components that form the controller for soil sampler 1000.

Figure 13:
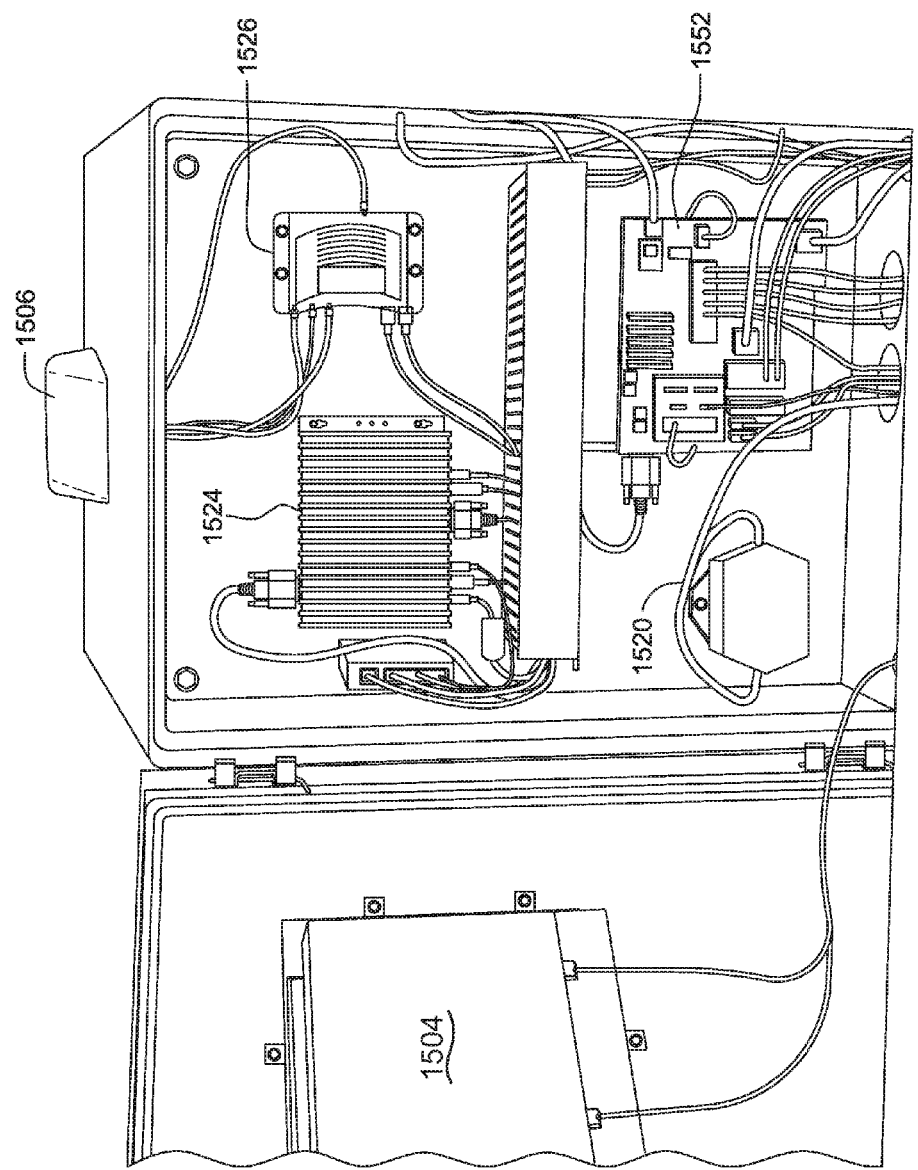
FIG. 13 is a side elevational, schematic view of an interior of the protruding electronics enclosure of FIG. 12.

Refer now also to FIG. 13. A communications module 1526 connected to external antenna 1506 provides integrated GPS, cellular and WiFi communications. The output of communications module 1506 is functionally connected to a custom electronics board 1522 that provides all specialized processing involved with operating and monitoring soil sampler 1000.

A general purposes computer 1524 handles routine processing tasks such as data logging, reporting, etc. Computer 1524 is operatively connected to custom electronics controller board 1522.

Figure 14:
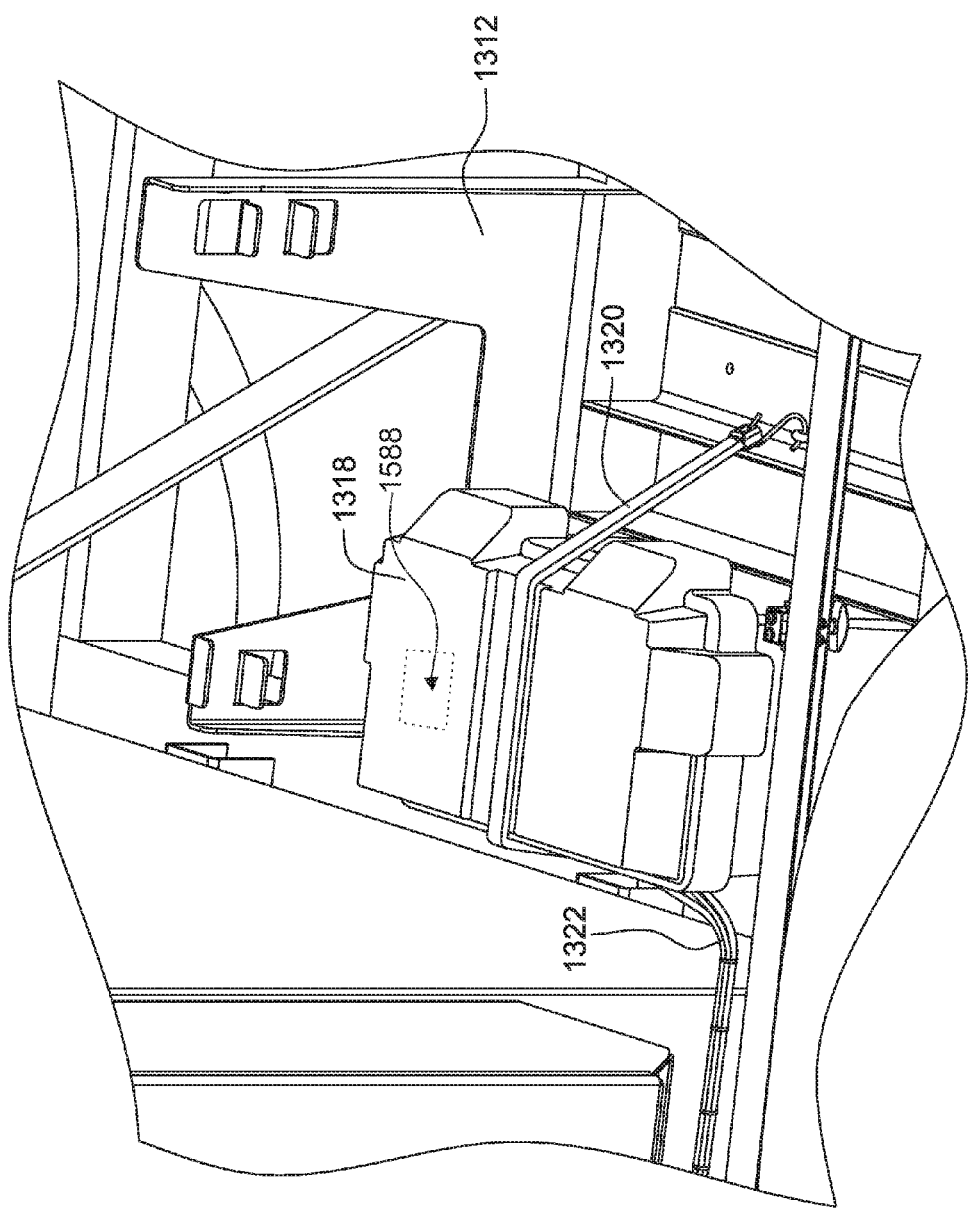
FIG. 14 is a side perspective, schematic view of a battery tray and battery case.

A trickle charger 1520 located in electronics enclosure 1302 is connected to one or more batteries 1528 located within battery cases 1318, best seen in FIG. 14. Because batteries 1528 are completely enclosed by battery cases 1318, consequently they are not visible in FIG. 14. Battery bases 1318 with enclosed batteries 1528 are disposed on battery shelf(s) 1312 attached to trailer frame 1002 below and forward of combined storage and electronics cabinet 1300.

A battery restraint 1320, typically formed from an elastic material, holds battery cases 1318 to battery shelf(s) 1312.

A display/control panel 1530 is disposed on the forward side 1308 of electronics enclosure 1302. Referring again also to FIG. 12, there is shown a right front perspective, schematic view of the front of electronics enclosure 1302 showing display/control panel 1530.

A large, bright warning light 1508 is disposed at the top of display/control panel 1530 so as to be visible in a side view mirror, not shown, of a vehicle towing soil sampler 1000. Warning light 1508 is illuminated when electronic controller detects an error condition.

Directly below warning light 1508 is a bright light for illuminating the working mechanisms of soil sampler 1000 to allow operation in low light conditions and providing adequate illumination so that forward facing camera 1512 can provide high quality images to the vehicle driver as discussed in more detail hereinbelow. Light 1508 is typically a multi-LED light assembly.

A forward facing camera 1512 provides an image of at least the sample carousel region as well as the sample extraction funnel 1202. The image from forward facing camera 1512 is available to the driver of the towing vehicle.

A series of electrical ports 1514 allow attaching diagnostic equipment to electronic controller 1502.

A voltmeter 1516 displays the state of charge of battery(s) 1528.

A master power switch 1518 allows completely shutting down soil sampler 1000.

An operator of soil sampler 1000 may monitor and/or control all operations of electronic controller 1502 from a computer, tablet, or similar Wi-Fi connected electronic appliance, none shown. All communication between the electronic appliance and electronic controller 1502 is via a Wi-Fi signal from multipurpose communications controller 1526. Typically, all functions available at touch screen 1504 are replicated on the Wi-Fi attached electronic appliance.

The Wi-Fi connected electronic appliance is also used to display images from forward facing camera 1512.

Referring now also to FIG. 14, there is a side perspective, schematic view of a battery tray 1312 supported on the frame of trailer 1002 just forward of combined electronics enclosure and storage cabinet 1300. One or more battery cases 1318, each typically containing a lead acid storage battery 1528, is held to battery tray 1312 with a restraint 1320. Battery shelf 1312 is sized and configures to hold two battery cases 1318. It will be recognized that battery shelf 1312 could alternately be configured to hold more than two battery cases 1318.

The one or more batteries are connected by a cable in cable bundle 1322 to electronics enclosure 1302. Trickle charger 1520 charges the batteries when soil sampler 1000 is connected to an external power source, typically 110/220 volt AC electrical mains. The one or more batteries allow self-powered operation of soil sampler 1000 when disconnected from the electrical mains.

The sophisticated on-board electronics (i.e., general purpose computer 1524, custom electronics controller board 1522, multipurpose communications controller 1526, etc.) allow a wide range of control, tracking, and reporting to be accomplished by soil sampler 1000.

All aspects of the sampling process are controlled by the on-board electronics. The number of samples (i.e., rotations of the sample collection drum 1102) before the samples are mixed and "dumped" into a sample collection container 1210 may be preprogrammed. As multiple probes 1174a etc. may be installed on sample collection drum 1102, more samples may be collected for each revolution of sample collection drum 1102. The control electronics may be programmed to allow for the multiple sample probes 1174a, etc.

As previously mentioned, bar codes of the sample collection containers 1210 may be pre-loaded into the control electronics. Signals from proximity sensors 1250a ... 1250d allow the control electronics to determine the angular orientation of collection assembly carousel platform 1128. The control electronics may reconcile the bar code on bar coded label 1218 to ensure that sample collection containers 1210 have been properly been placed in the sample collection tray 1212. Any discrepancy may be reported, primarily by an alert via error indicator lamp 1508. The tow vehicle driver may also be alerted via a message on the remote computer, tablet, or similar Wi-Fi connected electronic appliance, not specifically identified, typically located in the cab of the tow vehicle.

While no printer is typically included within soil sampler 1000, one may be provided in the vehicle cab or in any other appropriate spot. However, all operational information is transmitted to a "home base" where that data is collected and, when desired, analyzed using well known programs and/or techniques.

The onboard GPS facility allows tagging samples with, among other information, the latitude/longitude of the collection point.

The GPS facility allows location tracking the physical location of soil sampler 1000 whenever the electronics are powered.

Soil sampler 1000 provides remote usage logging through the onboard cellular communications facility. Among other possibilities excessive down time for extended breaks, etc. may be monitored.

The possibilities for other control functions and/or data collection and transmission will be readily apparent to a person of skill in the art. Consequently, the invention is not considered limited to the examples chosen for purposes of disclosure. Rather the invention is intended to include any and all other control functions and/or data collection/transmission operations within the scope of the disclosed invention.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. In a soil sampler system for collecting and retaining multiple soil samples, comprising: a mobile platform for traversing a region from which soil samples are to be periodically extracted; a hollow, sample collection drum supported upon and rotatively connected to said mobile platform, said drum having a central perimeter bearing a removable, outwardly projecting soil probe thereupon, said probe being communicative with an interior region of said hollow, cylindrical drum, said cylindrical drum having at least one mixing blade disposed on an interior perimeter thereof, and an opening in a first vertical side thereof to allow selective entrance of a distal end of a soil collection chute into an interior region of said cylindrical drum; a chute pivotally affixed to said mobile platform and movable between an operative position wherein a distal end of said chute is disposed within said interior portion of said hollow, cylindrical drum in a sample gathering orientation; and a non-sample gathering orientation external to said interior region of said hollow, cylindrical drum; means for receiving and individually retaining a plurality of said collected, blended soil samples disposed adjacent said chute; the improvement comprising:
   a) at least one flag affixed to a second, opposing vertical side of said hollow sample collecting drum and protruding outwardly therefrom;
   b) a sensor attached to said mobile platform proximate said flag, said sensor being adapted to generate an electrical signal as said flag passes said sensor as said hollow sample collecting drum rotates, said electrical signal being operatively connected to an electronic controller; and
   c) an electronic controller operatively connected to at least said sensor and adapted to count revolutions of said sample collection drum based upon input from said sensor.

2. The soil sampling system as recited in claim 1, the improvements further comprising:
   d) a row clearing apparatus disposed on said mobile platform forward of said removable, outwardly projecting soil probe and adapted to be selectively lowered and raised between a ground-engaging lower position and a non ground-engaging raised position.

3. The soil sampling system as recited in claim 2, wherein of said selective lowering and raising of said row clearing apparatus is accomplished by a cable having a first end operatively attached to said row clearing apparatus and a second end operatively to a lift arm connected to said sample collection drum such that said row clearing apparatus is raised when said lift arm is raised and lowered when said lift arm is lowered.

4. The soil sampling system as recited in claim 2, wherein of said selective lowering and raising of said row clearing apparatus is accomplished by an independent mechanism operatively connected to said row clearing apparatus and to a fixed portion of said mobile platform.

5. The soil sampling system as recited in claim 1, wherein said electronic controller is operatively connected to a drive system operatively connected to a sample collection funnel, said sample collection funnel is upon command from said electronic controller, selectively moved between a sample collecting position within said sample collection drum and a stored position outside said sample collection drum.

6. The soil sampling system as recited in claim 5, wherein said hollow cylindrical drum is supported on an axle retained in a pair of pillow blocks, said axle having a distal end centrally attached to said second opposing vertical side of said hollow cylindrical drum, and a proximal end having a pulley attached thereat; and an overridable clutch interposed between said proximal end and said distal end of said central axle.

7. The soil sampling system as recited in claim 1, wherein said electronic controller is operatively connected to a drive system operatively connected to a collection assembly carousel platform whereby, upon command from said electronic controller, said collection assembly carousel platform is rotated a predetermined number of degrees.

8. The soil sampling system as recited in claim 7, wherein said collection assembly carousel platform is adapted to receive, support, and retain a sample collection tray having a plurality of sample container compartments radially disposed therearound, each of said sample collection compartments being adapted to receive a sample collection container therein.

9. The soil sampling system as recited in claim 8, wherein each of said sample collection compartments have an opening in an outer perimeter to allow a bar code on a sample container placed therein to be scanned by a bar code reader external thereto, said bar code reader being operatively connected to said electronic controller.

10. The soil sampling system as recited in claim 8 wherein said collection assembly carousel platform comprises a hinged top selectively covering said sample collection tray, said hinged cover comprising an opening positioned to allow a mixed sample from said sample extraction funnel into one of said sample collection cups through said opening.

11. The soil sampling system as recited in claim 1, further comprising: at least one on-board electrical storage battery operatively connected to at least said electronic controller.

12. The soil sampling system as recited in claim 11, further comprising:

c) a communications controller operatively connected to said electronic controller and providing at least cellular and Wi-Fi connectivity.

13. The soil sampling system as recited in claim 12, wherein said communications controller further comprises a GPS receiver.

14. The soil sampling system as recited in claim 1 wherein said opening in said hinged cover comprises a slidable cover movable between an open position and a closed position.

15. The soil sampling system as recited in claim 1, further comprising:

c) a bracket affixed to said second, opposing vertical side and having an elongated slot in an outward facing surface, said elongated slot being configured to receive a locking pin therein; and d) a locking pin slidably affixed to said mobile platform and adapted to be moved between an engaged position in said elongated slot such that said hollow cylindrical drum is prevented from rotating, and a disengaged position such that said hollow cylindrical drum is free to rotate.

\* \* \* \* \*